(12) United States Patent  
Godschall et al.

(10) Patent No.: US 8,041,582 B2  
(45) Date of Patent: Oct. 18, 2011

(54) SYSTEM AND APPARATUS FOR MEDICAL ERROR MONITORING

(75) Inventors: Christopher Brian Godschall, Ellicott City, MD (US); Michael Treat VanSickler, Columbia, MD (US); Jill Vankirk, Tucson, AZ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 507 days.

(21) Appl. No.: 11/587,237

(22) PCT Filed: Apr. 28, 2005

(86) PCT No.: PCT/US2005/014429  
§ 371 (c)(1),  
(2), (4) Date: Oct. 31, 2008

(87) PCT Pub. No.: WO2005/111086  
PCT Pub. Date: Nov. 24, 2005

(65) Prior Publication Data  
US 2009/0048870 A1  Feb. 19, 2009

Related U.S. Application Data

(60) Provisional application No. 60/566,439, filed on Apr. 30, 2004, provisional application No. 60/571,434, filed on May 14, 2004, provisional application No. 60/575,244, filed on May 28, 2004.

(51) Int. Cl.  
*G06F 19/00* (2011.01)

(52) U.S. Cl. .......................................................... 705/3  
(58) Field of Classification Search ................... 705/2, 3  
See application file for complete search history.

(56) References Cited

U.S. PATENT DOCUMENTS

| | | | | |
|---|---|---|---|---|
| 2002/0169636 A1* | 11/2002 | Eggers et al. | ...................... | 705/3 |
| 2003/0055684 A1* | 3/2003 | Jaskolski et al. | .................. | 705/3 |
| 2003/0069759 A1* | 4/2003 | Smith | ................................ | 705/3 |
| 2004/0267562 A1* | 12/2004 | Fuhrer et al. | ...................... | 705/2 |

FOREIGN PATENT DOCUMENTS

AU  WO 2005/064578 A1 * 7/2005

* cited by examiner

*Primary Examiner* — Gerald J. O'Connor  
*Assistant Examiner* — John Pauls  
(74) *Attorney, Agent, or Firm* — Alexander J Burke

(57) ABSTRACT

An apparatus and system for providing improved monitoring errors in a medical setting. The apparatus includes a storage medium, display and scanner that allow medical personnel to quickly and reliably track and monitor samples collected from patients, such as information about the type, location, and timing of a collected sample. An unable to complete function labels incompletely collected samples or otherwise notifies the processing facility. Label sets and/or messages are generated to guide medical personnel when performing orders. Errors are linked to collection events for variance tracking. Temporary identifier labels are generated for containers and such when no order is pending. Order of draw procedures are communicated to medical personnel at the collection site.

21 Claims, 26 Drawing Sheets

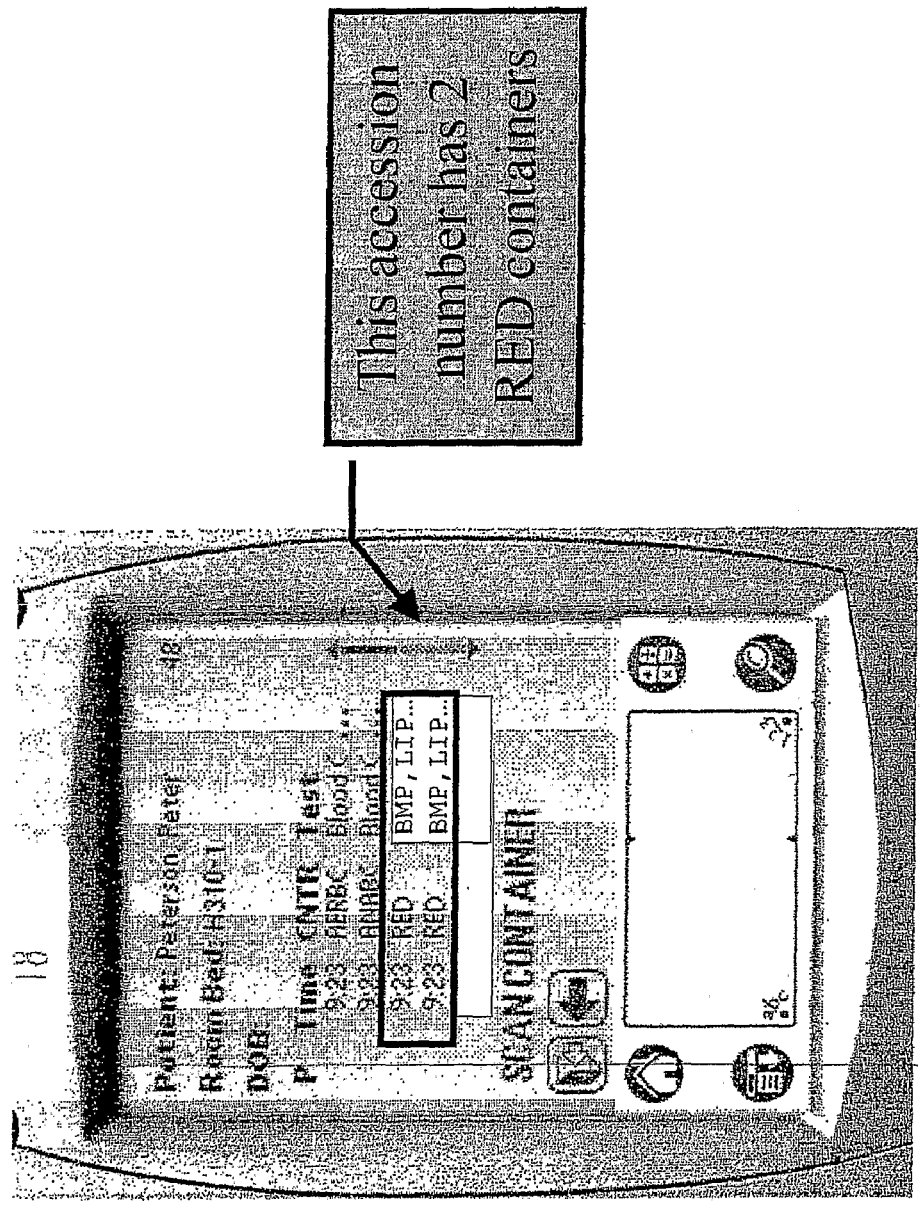

Pending Specimen Collections
Refreshes every 300 seconds... Refresh Now

Locations: A3

Total Patients: 7
Total Specimens: 29

Default Sort Order

STAT Pending Collections

| Cancel | Patient | Wristband | Scheduled | Location | Container | E | Test(s)-Special Instructions |
|---|---|---|---|---|---|---|---|
| ☐ | Thomas, Myra | M0009107 | 07 May 21:23 | A3/H311-2 | PURPLE | X | CBC |
| ☐ | Perez, Anita | M0009109 | 07 May 16:23 | A3/H315-1 | PURPLE | X | CBC Report Results to MD |
| ☐ | Perez, Anita | M0009109 | 07 May 16:23 | A3/H315-1 | RED | X | Lytes, Call MD with Results |

Routine Pending Collections

| Cancel | Patient | Wristband | Scheduled | Location | Container | E | Test(s)-Special Instructions |
|---|---|---|---|---|---|---|---|
| ☐ | Peterson, Peter | M0009106 | 08 May 09:23 | A3/H310-1 | AERBC | X | Blood Cultures |
| ☐ | Peterson, Peter | M0009106 | 08 May 09:23 | A3/H310-1 | ANABC | X | Blood Cultures |
| ☐ | Peterson, Peter | M0009106 | 08 May 09:23 | A3/H310-1 | BLUE | X | PT/PTT |
| ☐ | Peterson, Peter | M0009106 | 08 May 09:23 | A3/H310-1 | PURPLE | X | CBC, Diff |
| ☐ | Peterson, Peter | M0009106 | 08 May 09:23 | A3/H310-1 | PURPLE | X | CBC |
| ☐ | Peterson, Peter | M0009106 | 08 May 09:23 | A3/H310-1 | RED | X | Glucose |
| ☐ | Peterson, Peter | M0009106 | 08 May 09:23 | A3/H310-1 | RED | X | Lytes |

Pending Specimen Collections
Refreshes every 30 seconds – Refresh Now

Locations: All Locations

Total Patients: 9
Total Specimens: 29

Default Sort Order

STAT Pending Specimen Collection(s)

| Cancel | Patient | Wristband | Scheduled | Location | Container | E | Test(s) - Special Instructions |
|--------|---------|-----------|-----------|----------|-----------|---|-------------------------------|

Cancel Selected Orders

Select Order(s) then press the Cancel Selected Orders button on the bottom of the page.

SYSTEM AND APPARATUS FOR MEDICAL ERROR MONITORING

The present application claims the benefit of U.S. Provisional Application No. 60/575,244, filed on May 28, 2004; U.S. Provisional Application No. 60/571,434 filed May 14, 2005 and U.S. Provisional Application 60/566,439 filed on, Apr. 30, 2004 under 35 U.S.C. 119(e).

FIELD OF THE INVENTION

The present invention generally relates to remote networked medical error management devices, systems, and methods for using and operating the same. In particular, the present invention relates to a remote medical error management device having functionality to monitor, facilitate, and audit medical services.

BACKGROUND OF THE INVENTION

Laboratory Information Systems (LISs) and Hospital Information Systems (HISs) both fall under the category of Health Care Information or Enterprise Systems. Generally, health care enterprises provide various aspects of patient care such as patient identification and tracking, as well as medication and sample collection order and data management. In providing patient care, health care workers typically utilize one or more software applications accessible through a health care information system. Access to health care information systems have typically, in the past, required fixed terminals such as nurse workstations to be used at a location potentially distant from the point of care (i.e., at the patient's location). To provide more convenient and efficient access to an LIS, more portable modules such as handheld computers or portable data terminals (PDTs) have recently been introduced into health care and hospital settings and are hereinafter generally referred to as "handhelds". The handhelds can be connected to a server directly through a LAN, modem, or wireless connection. Optionally, the handhelds can be connected to a server through a PC using a serial or parallel connection. In order to use the handheld, the information on the handheld is synchronized with the LIS by connecting the handheld to a data import/export device connected with the LIS, or via a cable connected with the LIS, to allow the exchange of data between the LIS and the handheld.

In particular, portable computing devices utilizing software for medical error management are becoming increasingly common as medical healthcare technology improves. A portable computing device can collect clinical and non-clinical information about the sample collection process at a hospital, laboratory, or blood collection facility or clinic. To better manage patient-related testing results and the specimens from which those results were derived from, it is important to track the collected specimens and match them to the patient's identification information, which is typically stored in patient and specimen order databases such as hospital or laboratory information systems.

On occasion, a deviation might occur during the process of collecting samples from a patient. For instance, while collecting blood samples into blood collection containers, it is possible that a vein will collapse and the nurse or phlebotomist will not be able to collect all of the ordered collection containers that he or she has been instructed to complete. The containers, after being filled with blood samples, are typically put into a bag (one bag per patient) and subsequently delivered through a pneumatic tube system commonly found in hospitals. The pneumatic tube system will deliver the collected samples to the laboratory where the laboratory personnel gather and organize and sometimes even prioritize the samples for analysis on high-throughput analyzers.

If there was a problem collecting one of the tests samples ordered, it is the responsibility for the nurse or phlebotomist who performed the collection to notify the laboratory so that the laboratory personnel can appropriately address the situation. However, this step is often overlooked or forgotten, thereby likely requiring the laboratory technician to reorder the test for the same patient and possibly delay the analysis and results associated with that patient. The above-described inefficiency is time consuming and potentially dangerous if the doctor who ordered the tests needs the patient's clinical results in a timely fashion. It is also a discomfort to the patient as additional and potentially unnecessary sample collections are required due to lack of proper communication between the medical personnel involved in collecting and analyzing a sample. A need therefore exists for a medical error monitoring and management system that provides communication channels and/or means to notify a laboratory when less than all of the containers for an order are collected.

SUMMARY OF THE INVENTION

The proposed invention allows a hospital or laboratory technician such as a phlebotomist, doctor, or nurse to improve specimen collection order fulfillment and medical error monitoring.

An object of the present invention is to provide printed barcode labels that may be used to facilitate and complete the collection process and processing of medical tests. In accordance with an aspect of the present invention, the nurse or phlebotomist scans his or her own ID badge to identify themselves to the handheld. This part of the sample collection procedure is completed prior to the phlebotomist or nurse performing a specimen collection activity. Barcode scanning the patient along with the specimen collection containers intended for use facilitates the identification task associated with the collection process expeditiously, further reducing the time and inefficiencies associated with manually writing labels that are to be applied to containers or patient charts.

In accordance with another aspect of the present invention, a method is provided to acknowledge and record an exception event in data collection and allow an accurate recording and proper communication of an expected event that failed to occur. The present invention allows a hospital or laboratory technician such as a phlebotomist or nurse to quickly and conveniently communicate with a centralized laboratory in a hospital or other laboratory regarding a deviation in the completion of a specimen collection order. A preferred embodiment of the present invention enables an LIS to easily track and communicate sample collection deviations via barcode input or some other information. The basic components of a preferred embodiment of the present invention are a portable medical handheld device and miniature identification code reader. The identification code reader could be a barcode scanner, imager, radio frequency identification ("RFID"), infrared identification reader or similar technology. An example of such a portable computing device is the Symbol Technologies PPT 1800 Series Pocket PC. The handheld comprises features that include bar code scanning and real-time wireless communication options.

The subcomponents of the medical handheld device may be a battery, display, keyboard, cradle, wireless communications circuitry, memory, housing, and central processing unit (CPU). The medical handheld device can be any portable diagnostic monitor such as a portable data assistant (PDA), notebook computer, tablet PC, or other device. An identification code reader can be integrated into the medical handheld device or attached to the medical handheld device via an accessory device. The reader could potentially be detachable to the portable computing device.

Along with carrying the portable medical computing device, which may have a reader attached or integrated inside, a nurse or phlebotomist can also carry a portable printer for printing barcodes at the site of patient sample collection. In a preferred embodiment, blood collection containers are used which include a barcode having tube-specific information to be registered with the handheld of the present invention. For example, a plurality of collection containers such as blood collection tubes, blood culture bottles, and the like could have a two-dimensional barcode that provides information about the type of collection container such as catalog number, expiration date, and reorder number.

Under certain circumstances, a collection exception event involves an order with more than one of the same type of container. In accordance with a further aspect of the present invention, an Unable to Complete Collection (UTC) feature provides communication of uncollected event data from the handheld to a laboratory and the LIS when collection using one or more of the same type of container is unsuccessful. This feature assists in determining the necessity of collecting additional data if successful event recordings provide enough information invalidating the need. In the hospital environment, when a patient blood collection order has been introduced to the Laboratory Information System, the order might call for identical samples to be collected for additional testing volume of patient sample. However, if the additional identical sample could not be collected based on an unexpected situation, i.e. vein collapse, patient refusal to provide draw of blood, other emergency, etc., the proposed invention herein provides a feature to alert the laboratory personnel of the error. As the laboratory personnel will be informed about the status of an order whether successful or not, this feature will reduce, or in some instances eliminate, poor communication between the clinician and laboratory. Laboratory personnel, upon recognizing an event exception, can quickly determine if the successful specimen collections obtained provide sufficient sample for the required test or tests and appropriately address the situation. Without proper communication from the clinician, the laboratory personnel might be required to reorder the entire specimen collection based on incomplete information provided, causing analysis delays which leads to treatment delays.

BRIEF DESCRIPTION OF THE DRAWINGS

These and other aspects, advantages and novel features of the present invention will be readily comprehended from the following detailed description when read in conjunction with the accompanying drawings:

FIG. 5 depicts a client handheld configured, in accordance with an embodiment of the present invention, in use with a specimen container and corresponding bar code label; and FIGS. 6 through 14 depict respective client handhelds with exemplary display screens, in accordance with an embodiment of the present invention;

FIGS. 16 through 26 depict different web pages generated by a system web interface, in accordance with an embodiment of the present invention;

DETAILED DESCRIPTION OF THE PREFERRED EMBODIMENTS

Figure 1:
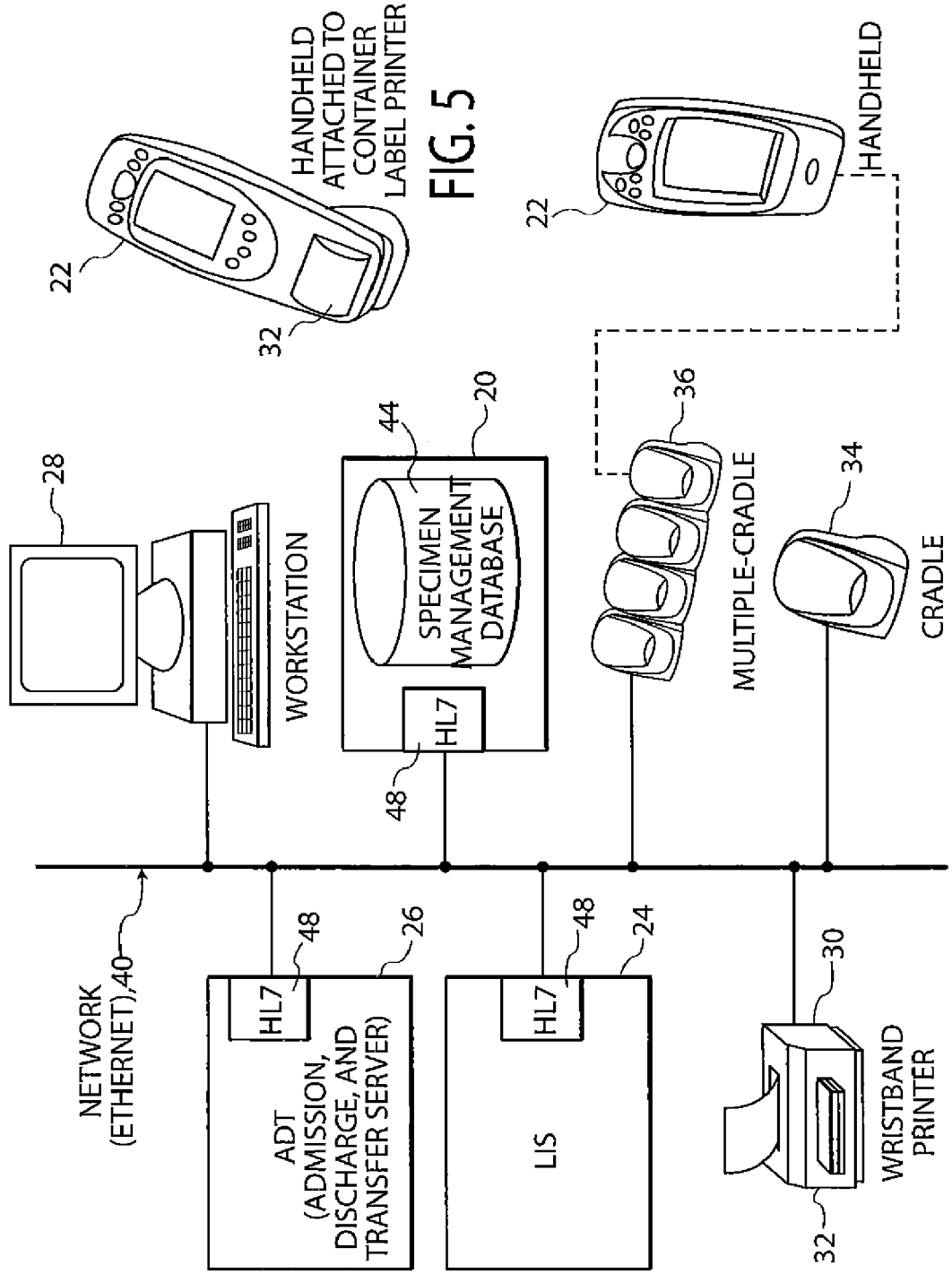
FIGS. 1, 2, 3 and 4 each illustrate a client handheld(s) and server configured, in accordance with different embodiments of the present invention, in use with different configurations of a health care information or enterprise system.

In accordance with the present invention, an error monitoring and management system 10 (FIG. 1) and portable medical device 22 (FIG. 5) are provided. The device 22 uses handheld scanners for specimen collection procedures, similar to those commonly done in hospitals. For illustrative purposes, the system 10 and device 22 will be described herein with reference to specimen collection procedures. It is to be understood that the system 10 and the devices 22 can also be used for monitoring the administering of therapeutics to patients, among other similar applications. The system 10 can be the BD.id system available from Becton Dickinson and Company, Franklin Lakes, N.J.

The handheld or PDT 22 (FIG. 5) allows a user such as a nurse or phlebotomist to match the specimen collection orders stored in the handheld 22 with the information scanned from the patient wristband, and to confirm that the specimen container 56 is the correct one for the tests ordered. A new bar code label 52 for the specimen container is printed at the patient's bedside with the time and date of collection. The label can be placed on the collection container, the patient's chart, or both. Additionally, the information about the time and date a container is collected can be electronically transmitted to a data storage element (e.g., the LIS 24 or SMS 20) for retrieval at a later time. Lastly, when replaced in its cradle 34, the handheld synchronizes with the SMS 44, which is then able to communicate with the LIS 24.

As will be described in further detail below, one of the features of the system 10, in accordance with an embodiment of the present invention, involves communication between the user and the handheld 22 that there has been a deviation in the order of collection performed by the phlebotomist. This deviation can take a number of different forms. Most importantly, a button on a handheld 22 or a portion of the screen on the handheld 22 are reserved for the user to communicate to the handheld that the deviation has occurred. With reference to FIGS. 1 through 4, the system 10 preferably comprises a server 20 (e.g., a specimen management server (SMS)), a plurality of client handhelds 22 with data accessibility to the server 20, a LIS (Laboratory Information System) 24, and an ADT (Admission, Discharge, and Transfer system) 26. The system components are connected to a network 40 to allow for specific communication events to occur. Other embodiments might include aspects of the server 20 embedded into the LIS 24 instead. The handhelds 22 can communicate with hospital computer systems (e.g., the LIS, ADT and HIS) via the server 20. Alternatively, the LIS, for example, can be configured to communicate directly with the handhelds 22. To understand the present invention, certain terms shall be defined as follows:

DEFINITIONS

Client

The client 22 is the handheld device that can download files and data for manipulation, run applications, or request application-based services from a file server.

Cradle

A cradle 34 is a docking station used to provide an interface with a host terminal. The cradle 34 can be adapted to receive and secure the handheld 22. A detector element can be included to detect when the handheld 22 is placed in the cradle. Data can be received from a server 20 and selectively downloaded when the handheld is placed in the cradle. In one embodiment of the present invention, the server 20 is a SMS. An actuator on the handheld can be employed for initiating the transfer of data to a process in the host terminal if the detector indicates that the handheld 22 has been placed in the cradle 34.

Collection Container Label Printer

The collection container label printer 32 is a printer intended for printing labels at the point of use, such as the location of sample collection. More specifically, in certain locations within the healthcare setting, collection container label printers are needed for printing labels with indicia of the collected sample for downstream tracking and processing of the sample, such as which patient the sample was taken from, and other information useful for the healthcare worker or laboratory technician. An important element on the collection labels is the container number (e.g., barcode), which can generally be described as the collection identification number. Ideally blood collection containers 56 (FIG. 5) would be available to the health care worker including a barcode 52 or RFID (radio frequency identification) tag communicating tube specific information to be registered with the portable handheld device 22 of the present invention. In one embodiment, the barcode label 52 is printed upon scanning of a collection container's barcode after the user and patient have both been scanned into the system. The barcode printer 32 can be located or housed on a phlebotomy cart or tray, or mounted in a patient's room or the like. The printer 32 creates a customized label 52 containing the bar code accession number that the LIS 24 has assigned to the specimen. The printer 32 may be a portable printer such as a battery-powered thermal printer.

Database

The term database (e.g., the specimen management database (SMD) 44) includes one or more large structured sets of persistent data, usually associated with software to update, insert, and query the data.

Handheld

The term handheld (e.g., client handheld 22) describes portable computers useful for executing specimen or medication management at the point of use. An example of such a portable handheld element is the Symbol Technologies PPT 1700 Series handheld. This specific handheld has IR and barcode scanning capabilities. The handheld comprises a graphical user interface (GUI) for displaying information useful for collecting specimen samples from a patient.

Preferably, the handheld includes a microprocessor, reading element such as a bar code scanner, and printing element. The reading element is capable of reading identification information from a patient identification code and producing a corresponding information label. The microprocessor is capable of processing data relating to the identification information. The handheld ideally comprises a miniature identification code reader. The identification code reader could be a barcode scanner, imager, infrared identification reader, RFID reader or similar technology. A barcode scanner could be integrated into the medical handheld device or attached to the medical handheld device via an accessory device. Likewise, an RFID reader could be integrated into the medical handheld device so that when in the proximity of the container the container's RFID could be read by the reader. The handheld preferably includes a battery, a display screen for the GUI, depressible keys, communication circuitry, a memory element, a housing for securing all the handheld subcomponents, and a microprocessor. The portable handheld device could be a portable digital assistant (PDA), tablet PC, or notebook computer that includes a module and/or software for communicating with a server.

HIS

The Hospital Information System (HIS) 38 (FIG. 2) is a system developed with the objective of managing and streamlining the treatment flow of a patient in the hospital, along with all data associated with the patient necessary for efficient and organized healthcare service. Treatment flow includes, but is not limited to, specimen management and medication management. The HIS allows doctors and other staff to perform to their peak ability in an optimized and efficient manner. Most HISs are modular, thus ensuring sustained benefits through changes in technology such as integration with new and improved LIS and ADT systems 24 and 26.

HISs 38 use a network of computers to gather, process, and retrieve patient care and administrative information for most hospital activities to satisfy the functional requirement of the users. HISs also help to provide decision support systems for hospital authorities developing and managing comprehensive health care policies.

HISs 38 incorporate integrated computerized clinical information systems for improved hospital administration and patient health care. They also provide for accurate, electronically stored medical records for one or many patients. Typically, HISs are centralized information systems designed for quick delivery of operational and administrative information and include software capable of optimizing core data and other application modules customizable to the hospital or healthcare facility.

LIS

The term LIS 24 preferably defines a computer network comprised of industry standard network hardware and software (network and communication protocols) that serves to allow communication between the patient health record repository, the end-user client applications running on various device types, and the various types of servers. This network can take the form of a cable-based or fiber optic network, a local area network (LAN), a wide area network (WAN), a virtual private network (VPN), the Internet, or any other type of network that allows communication between computing devices.

The LIS typically is limited to laboratory information systems that organize and track information pertaining to laboratory tasks such as how orders are generated and communicated to the lab, how patients or samples are delivered, how the samples are accessioned and prepared, how testing is actually accomplished, and how results are communicated to healthcare providers. LISs can also organize, track, and determine how the health enterprise is reimbursed for the work done in the lab, and how the reimbursement information is exchanged.

Figure 2:
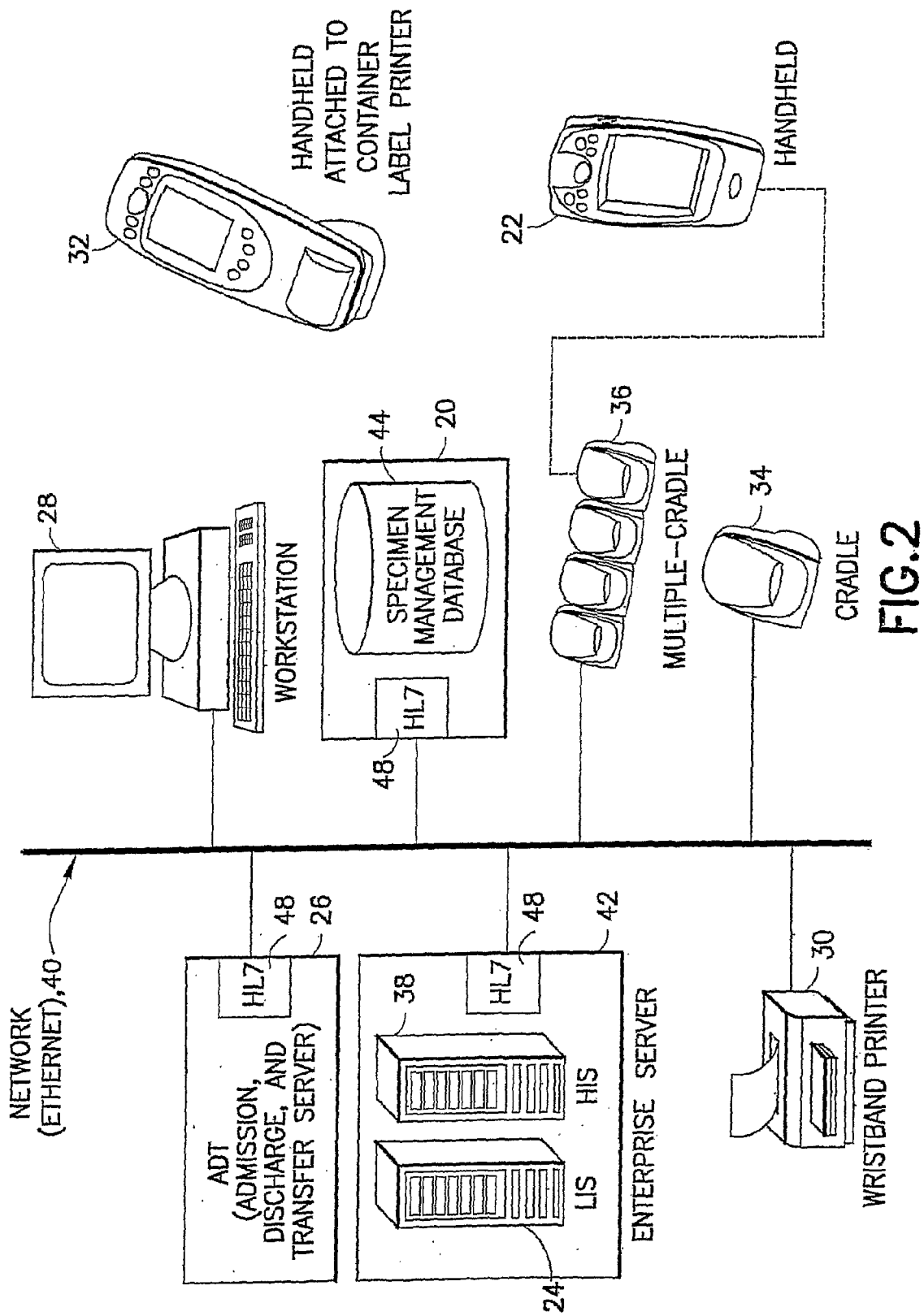
Figure 3:
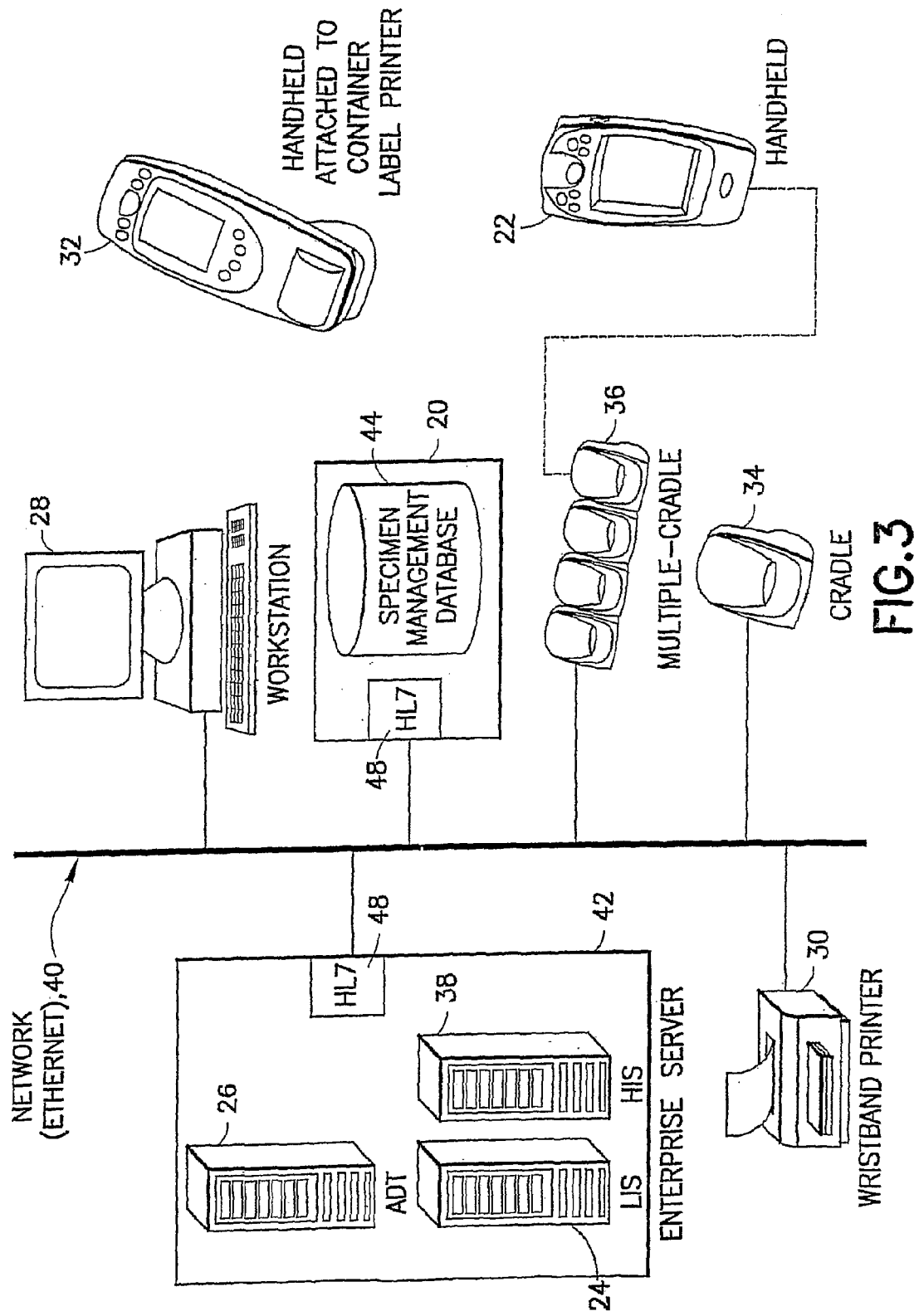
Figure 4:
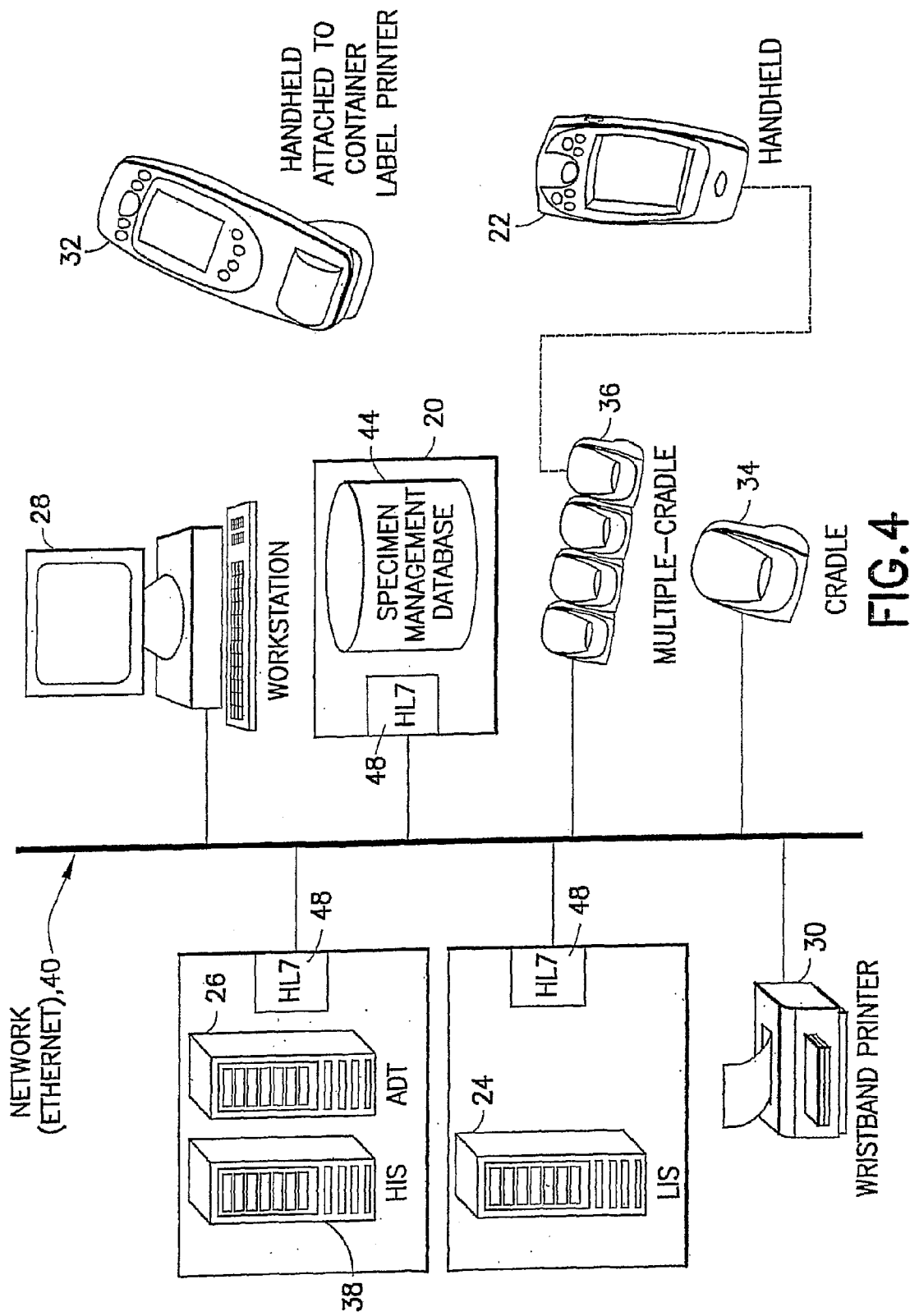

As shown in FIG. 2, an enterprise server 42 can comprise the LIS 24 and the HIS 38, or the ADT 26, LIS 24 and the HIS 38, as shown in FIG. 3. Alternatively, the HIS 38 and the ADT 26 operations can be combined in a single server (FIG. 4), among other configurations. In the system 10 of the present invention, the LIS has a bi-directional interface with the server 10 to allow collection lists to be sent from the LIS to the server 20, and to allow collection data and canceled orders to be sent from the server 10 to the LIS.

LIS/HIS Data Interface

The LIS/HIS data interface 48 is an element for allowing for facilitated communication for multiple modules sending and receiving data packets and signals across a network. Examples include Health Level Seven (i.e. HL7 3.0), ASTM 1238, ASTM 1394, Dbase, Comma Delimited ASCII, and Fixed Length ASCII.

Patient ID Printer

The patient ID printer 30 is a printer typically designated for printing patient ID tags such as wristbands critical for accurate and efficient patient identification and safety. Patient ID tag printers are usually connected to a network and communicate with the ADT and HIS systems 26 and 38. Devices can also be provided to produce RFIDs along with the barcodes.

Specimen Management Server

The specimen management server (SMS) is a server 20 comprising a database and other programs and modules 60 (FIG. 6) for running and integrating LIS 24, HIS 38, and client handheld systems 22 (e.g., a web server, a SQL server, a LIS to SQL parsing application, and so on). Typically, the specimen management server 20 creates and updates its database with information specific to patients and specimen samples collected from those patients. The specimen management server 20 in some embodiments is capable of executing a replication/synchronization service to maintain intermittent communication with the client 22. In some embodiments of the present invention, functionality of the specimen management server 20 can be integral to the LIS 24, HIS 38, or both. In other embodiments of the present invention, the SMS 20 can be separate from the LIS 24 and HIS 38, but run on the same network as the LIS 24 in order to receive updated information related to sample orders and accession numbers generated through the LIS 24.

Unable to Complete Collection (UTC) Function

Figure 7:
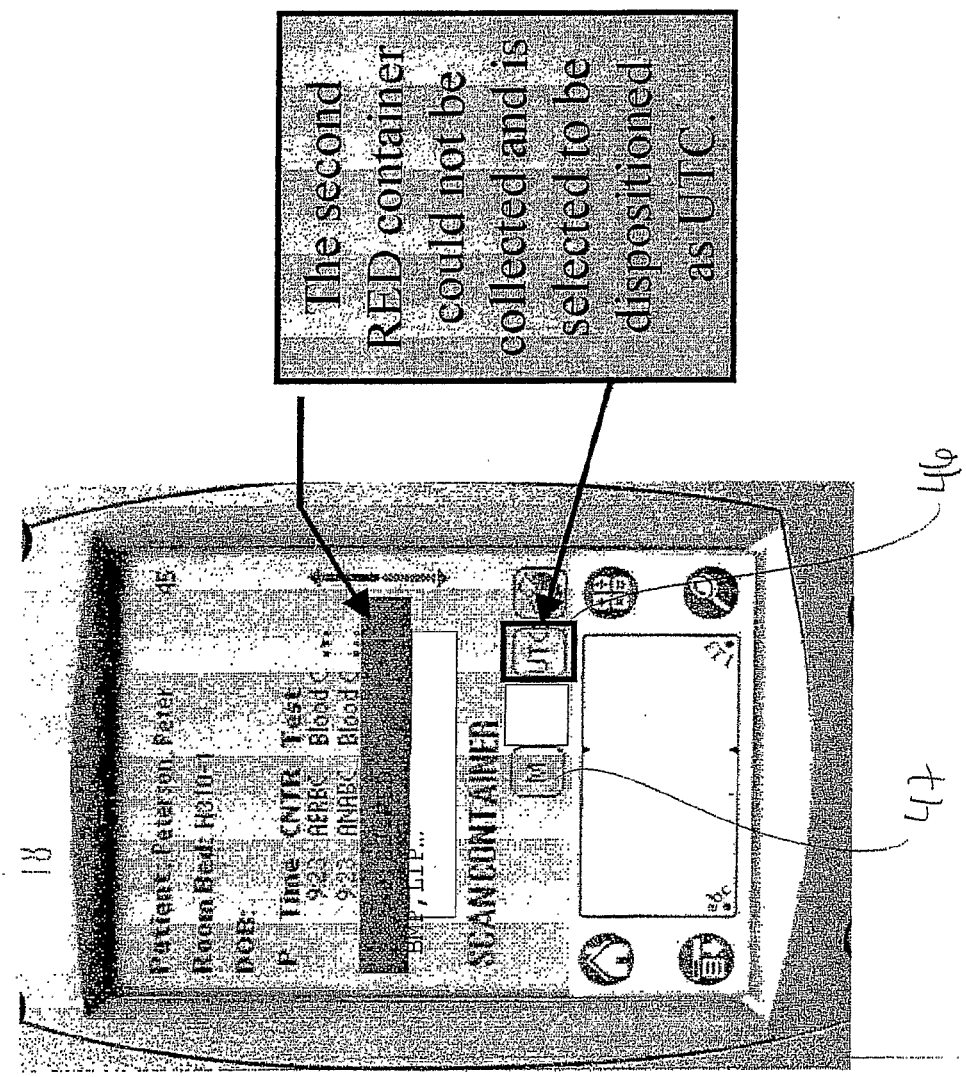

The Unable to Complete Collection (UTC) function is illustrated in FIG. 7 as a "UTC" icon 46 on the display 23 of a handheld 22, and represents "Unable to Complete Collection." This disposition status is used when there are multiple containers of the same type and one or more could not be collected. When two or more of the same container type exist on an accession number and one of the containers is not collected, the uncollected container is dispositioned as UTC. A system parameter can be set to control if a label prints for the uncollected container. This label provides information to the laboratory as to the collection status of the order. The uncollected container(s) cannot be "cancelled" because the laboratory needs to assess whether or not the test(s) can be performed on the specimen that is collected. To disposition a test as UTC, the user selects the container and taps the UTC button on the handheld display. A label prints if the system parameter for printing this label is activated.

The Unable to Collect Collection (UTC) feature of the present invention will now be described. To better illustrate the advantages of a system 10 and/or handhelds 22 that employ the UTC feature over existing medical error monitoring systems and devices, a description of how these existing medical error monitoring systems and devices process incomplete collection scenarios will first be provided.

The LIS/HIS assigns accession numbers to orders made by qualified medical personnel for sample collections. The method of assigning accession numbers and test data vary among LIS providers. When a doctor or other qualified medical personnel calls for specific tests for a patient, typically each test required demands at least part of a single collection container for the patient sample. However, some tests require multiple containers for the same test order to accommodate the analysis methodology or simply to provide enough sample volume. In a first example, it is possible that two dissimilar containers are required to collect and contain the sample for the same test order. In a second example, a single test order might call for two identical containers to maintain the collected sample for volume purposes. LISs also do some grouping such that tests that require the same collection container will be combined such that, for example, 4 tests that each require a RED10 container would use "volume required" data to determine if the 4 tests can be run from a single container or if multiple containers are required.

Depending on the LIS manufacturer used by the healthcare facility, each test might be assigned an individual accession number or, in other cases, one accession number might be assigned to the set of tests required of a patient. This poses a problem for existing error management devices with regard to communication to the LIS since only a single message may be relayed to the LIS concerning the status of a single test order (i.e., the order must be completed, not completed, or cancelled). With some existing LIS manufactures, there is no way to say that a test order was not completed. When a nurse or phlebotomist messages back to the LIS, he or she needs to have some status associated with each test order; otherwise, the LIS assumes the order was collected or canceled, depending on the message format.

For a typical test, only one collection container is used. Given successful conditions, the user should be able to collect the sample and have it recorded by the error management system and proceed to the next test or patient. The successful collection is then reported to the LIS (e.g., the PDT is synchronized with the LIS through the HL7 interface). If for some reason the test is no longer necessary, as determined by qualified medical personnel, the user has the ability to cancel the test on the PDT which, in turn, informs the LIS of the cancellation. If an event occurs which prevents the user from completing a required single tube collection order at the present time, the user may choose to defer the test to a later time. In this case, the PDT maintains the test information in its memory and allows the user to return to the test at a later time. If a user skips an entire accession number, thus leaving it around for a later collection, no message is sent to the LIS. No action being performed is a non-event to the LIS. Existing LISs are configured to only be informed when a test is collected or canceled.

In a test that requires two or more collection containers, given an exception event after collection of the first sample, an existing PDT cannot communicate to the LIS that one or more containers have been collected and that one or more have not. This is because current LIS systems force a collection standard defined by messaging a single result of the exam for a single accession number. Therefore, an existing PDT cannot communicate two results for a test within the same accession number requiring multiple samples. The present system and provide a solution to this limitation of the LIS.

An embodiment of the present invention provides a means of generating a message that can be sent to the laboratory staff indicating that one or more collection containers were not successfully collected. This presents the user with the options of collecting the order, canceling the order, deferring the order, or designating an order as unable to be collected given the test circumstances within the same accession number. The error management device (e.g., the handheld 22) is able to evaluate the status of the blood collection order and provide the proper options for the user to choose from. The method of providing such options can be made in the display 23 (FIG. 5) of the portable computing device 22 (e.g., the UTC touchscreen button 46 in FIG. 7), or by means of a mechanical button or toggle switch on the handheld 22, among other options.

Referring to FIGS. 6 through 14, different screen displays are shown in accordance with an embodiment of a portable medical device or handheld 22. The handheld 22 can be used by nurses or doctors for management of specimen collection samples. The term "user" is used herein to describe a person who uses a handheld to track samples of specimens collected from patients, especially in the healthcare setting.

The handheld 22 is able to receive input data via a information code reader; such as a barcode reader. Input data can include, but is not limited to, codes or other indicia existent on sample collection containers, patient ID tags, and health practitioner personnel tags. For example, the system 10 and handheld 22 are configured such that a user can remove the handheld 22 from its cradle 34 and then scan his or her ID badge to communicate to the handheld 22 who is currently using the device and who will be performing the collection of specimen samples within a given hospital ward, section, or floor. The scanner can be integrated in the handheld. Alternatively, a handheld 22 can be secured to a sled accessory that contains a barcode scanner. The sled accessory can have latching mechanisms to allow a user to removably the secure sled accessory to the handheld 22. When the two components are secured together, a communications port on the sled accessory engages with a similar port on the back of handheld 22 to transfer data and information between the two components.

The handheld further comprises a display 23 such as a liquid crystal display for displaying information of the devices for the user to see. Additionally, the display 23 can be of the sort that is used with fingers or a touch pen pressing on the display for executing related commands.

The handheld 22 also includes internal memory for recording the results of a collection and the date and time of collection, as well as the orders assigned to the handheld 22. In one embodiment, handheld 22 has a communications link for downloading or synchronizing the completed tests that were ordered and stored in handheld 22. As described in further detail below, the tests can also be dispositioned as canceled or part of a UTC operation. The communications link may be a wireless link or a hard wire connection. The information may be downloaded or synchronized to a computer associated with the ward or floor in a hospital, or a laboratory information system overall.

A screen (not shown) on the display 23 can provide a list of patients assigned by the system administrator to the handheld 23 for collections. A web interface to the server 20 is described below in connection with FIGS. 16 through 29 which facilitates system administrator operations. The user then selects a patient from the list to view a new screen that lists the tests ordered for that patient, as shown in FIG. 6. In the illustrated example, an order was made to perform a number of collections for a fictitious patient "Peter Peterson". The screen in FIG. 6 prompts the user to scan the containers for a particular accession number. The user does so by placing the collection tube in the near vicinity of the scanner, as shown in FIG. 5.

Figure 9:
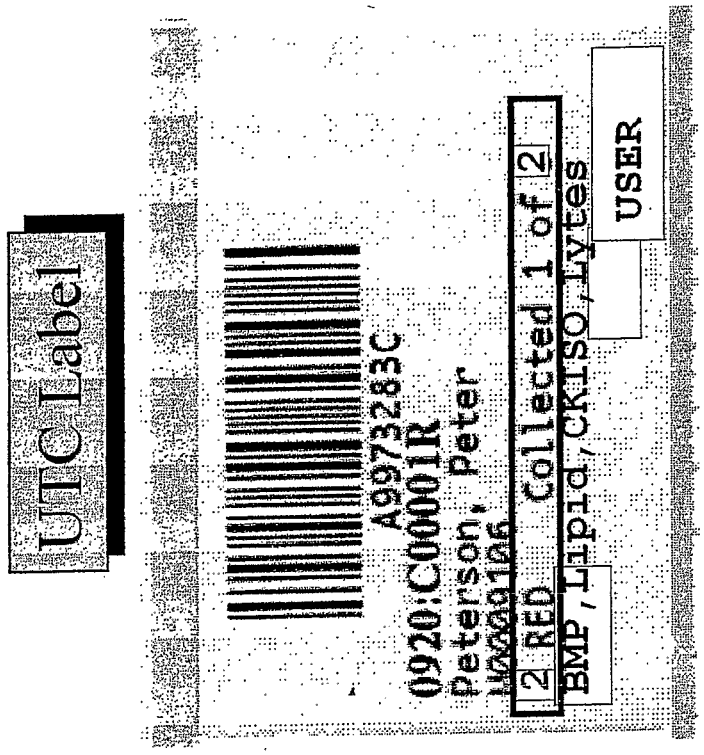
Figure 8:
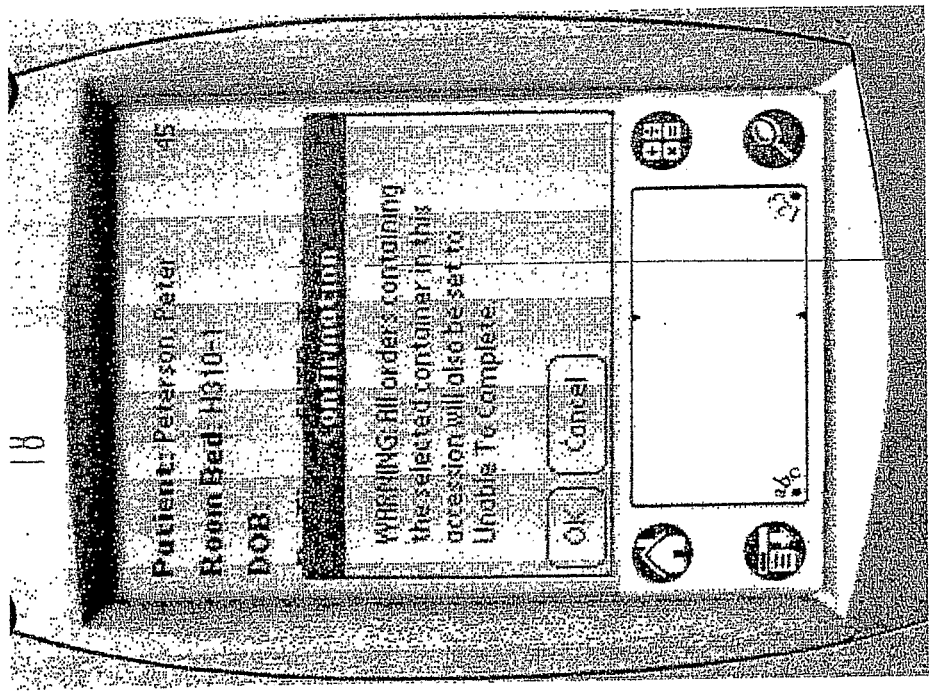

FIG. 6 illustrates a handheld screen for a test wherein an accession number has two of the same type of containers (i.e., RED) associated with it. With reference to FIGS. 7, 8 and 9, in the event that a multiple container test cannot be completed (i.e., not all of the RED containers are successfully collected), the handheld 22 can display a message (FIG. 8) that the containers in the order will be dispositioned as UTC since the user was not able to collect a specimen. Further, the handheld 22 can generate a command to print a label (FIG. 9) that can be attached to or inserted in a bag that is sent to the lab. Upon receiving the bag, the laboratory technician would be able to read the sample and identify that there was a sample collection deviation. The laboratory personnel could then further order an additional test (and the collection containers associated with the test), or use the samples that reached the laboratory and possibly allocate a portion of the specimen from those containers to perform the necessary test. Furthermore, the message could be sent directly to the laboratory for the laboratory personnel to make the appropriate test decisions in preparation for the collection specimens that were originally supposed to arrive at the lab. Notification could be sent via a wireless communications circuitry within handheld 22 or optionally through synchronization with the server while in a cradle.

Figure 15:
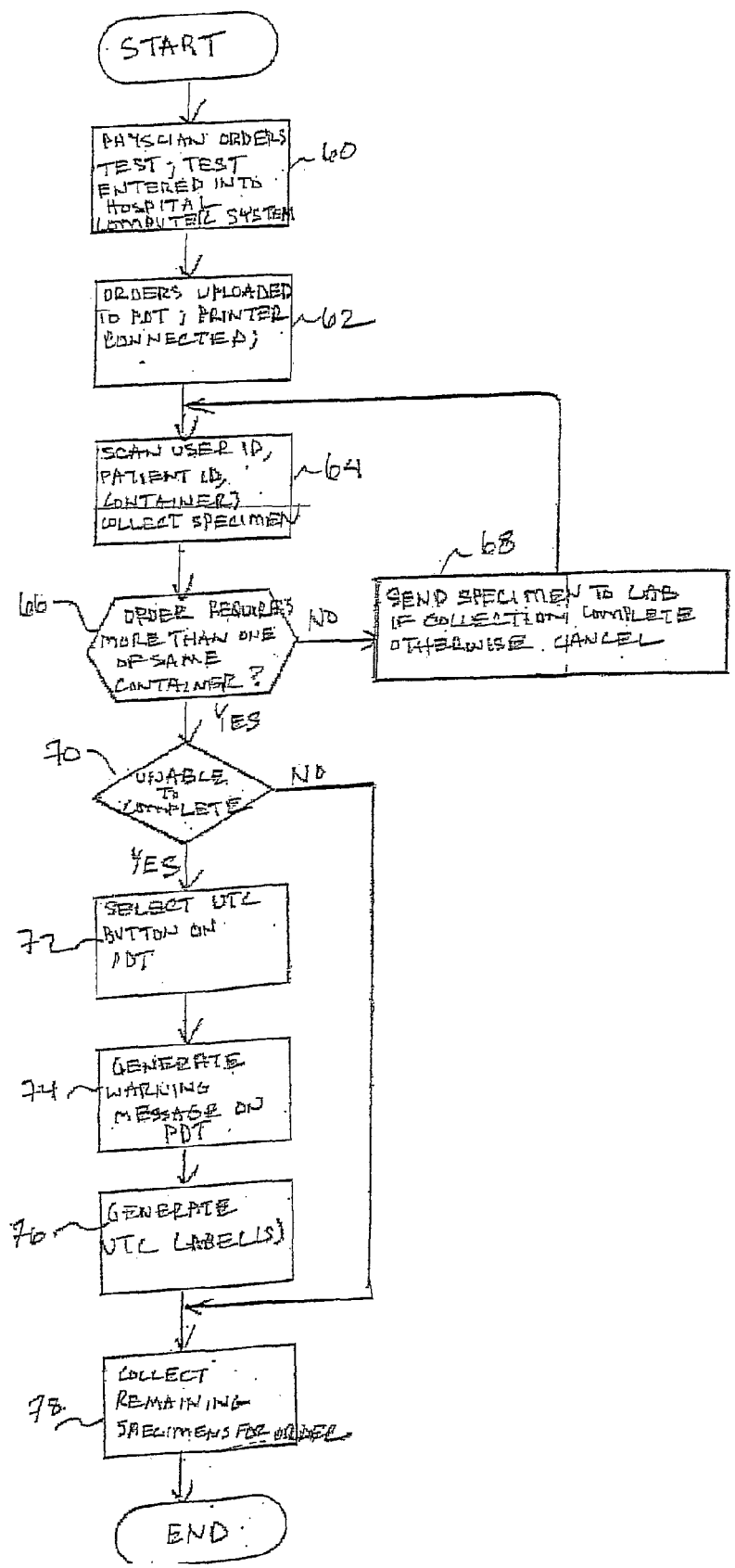
FIG. 15 is a flow chart depicting a sequence of operations for controlling a client handheld(s) when an order cannot be completed in accordance with an embodiment of the present invention.
Figure 17:
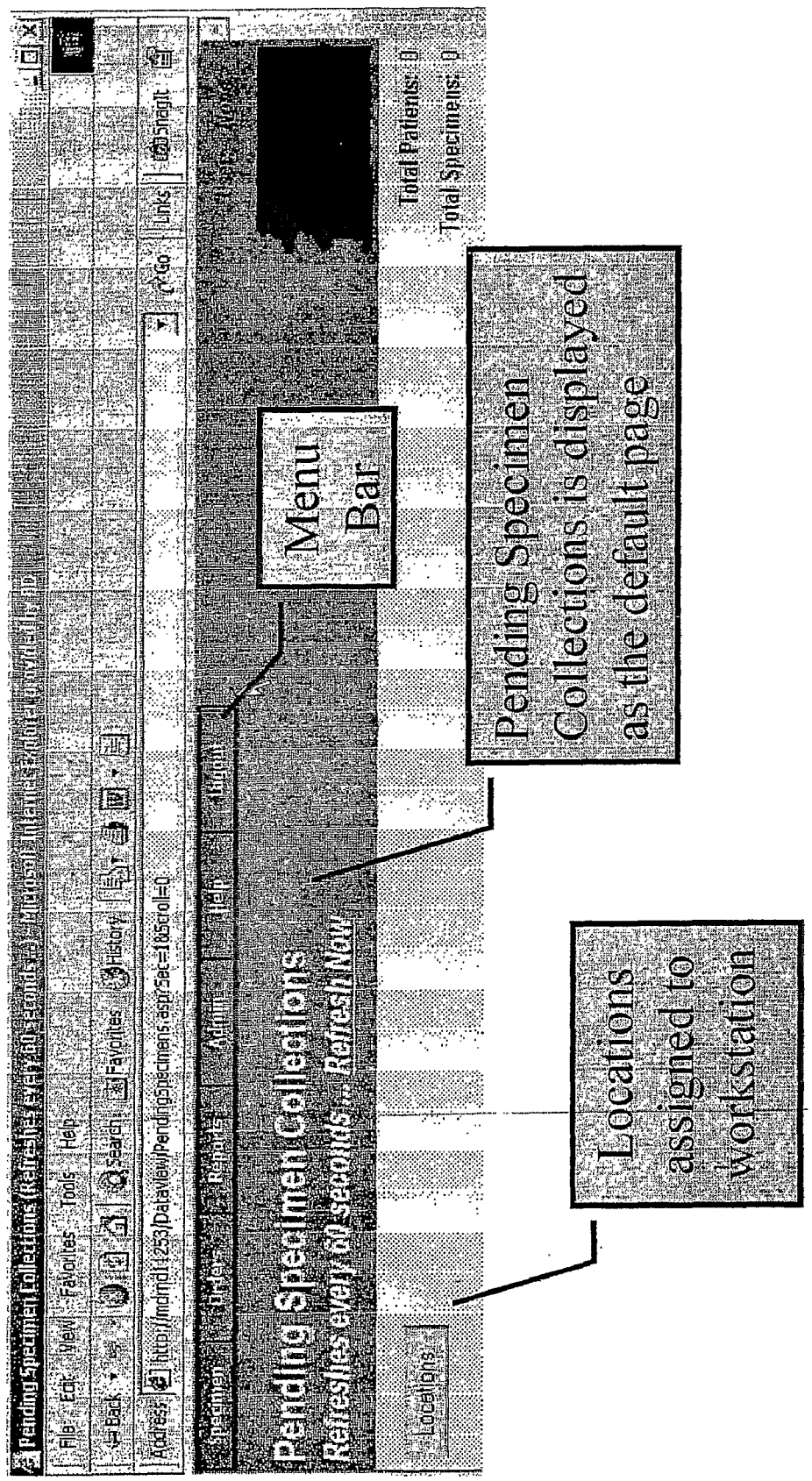
Figure 18:
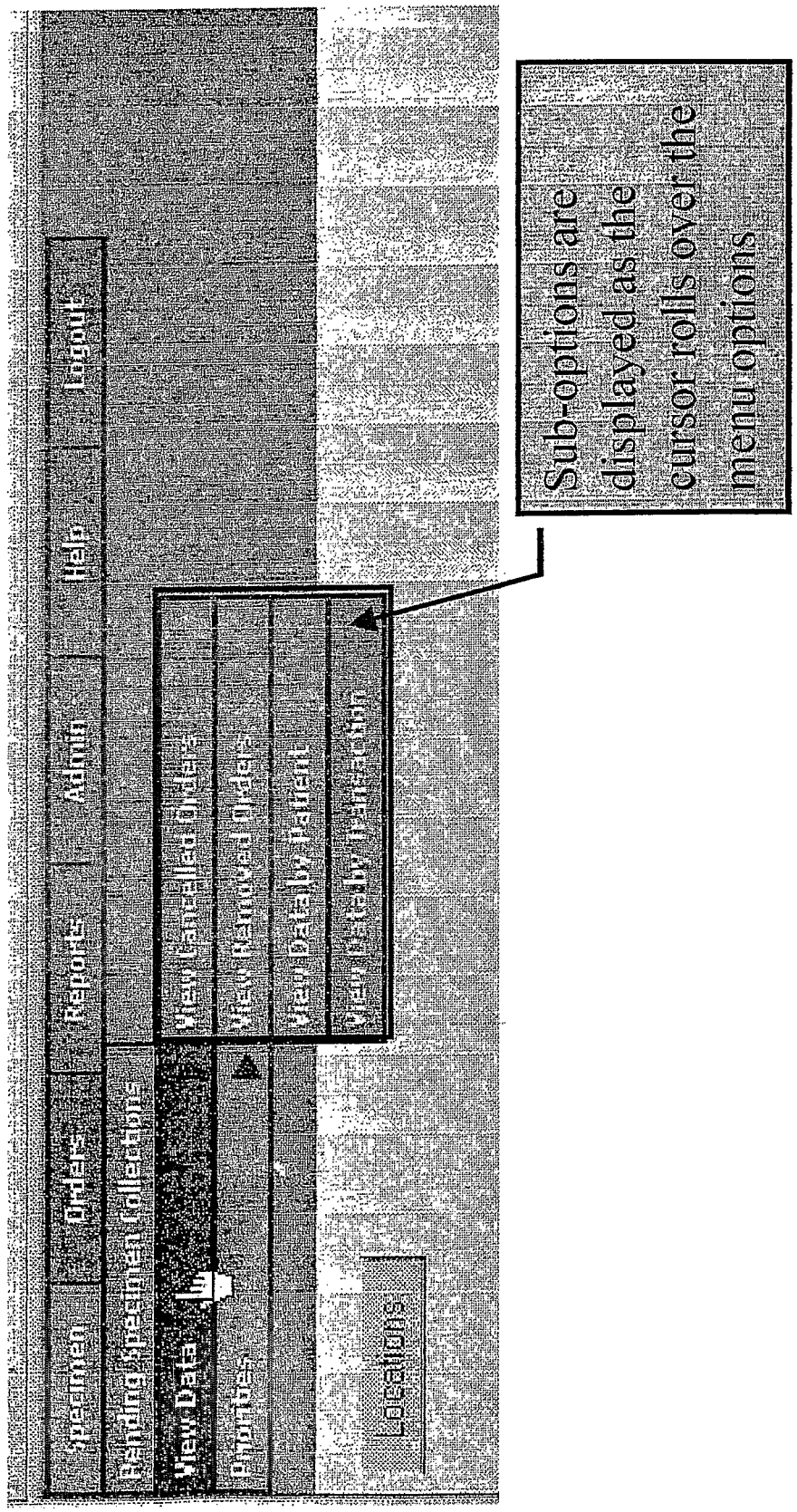
Figure 19:
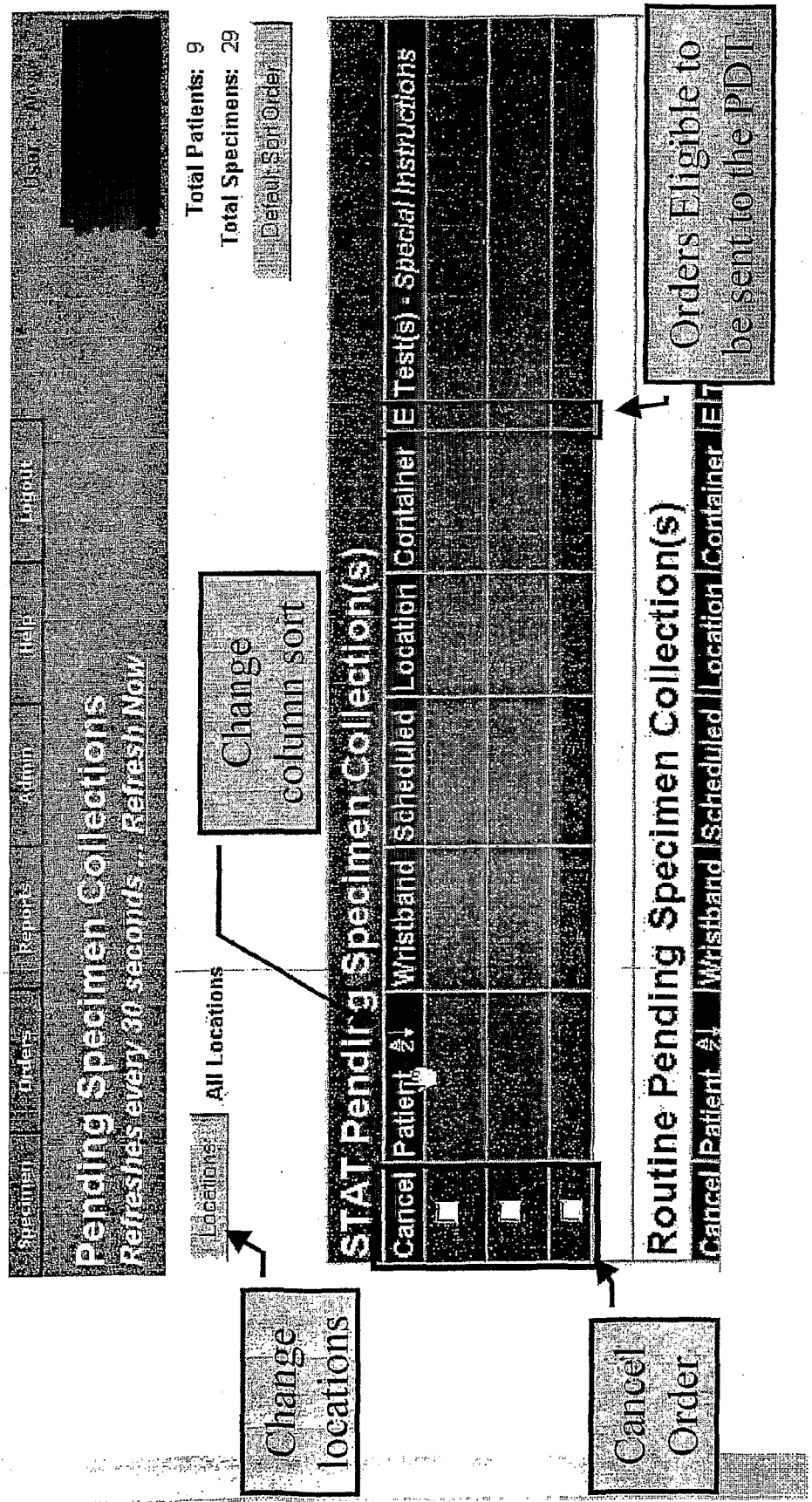
Figure 20:
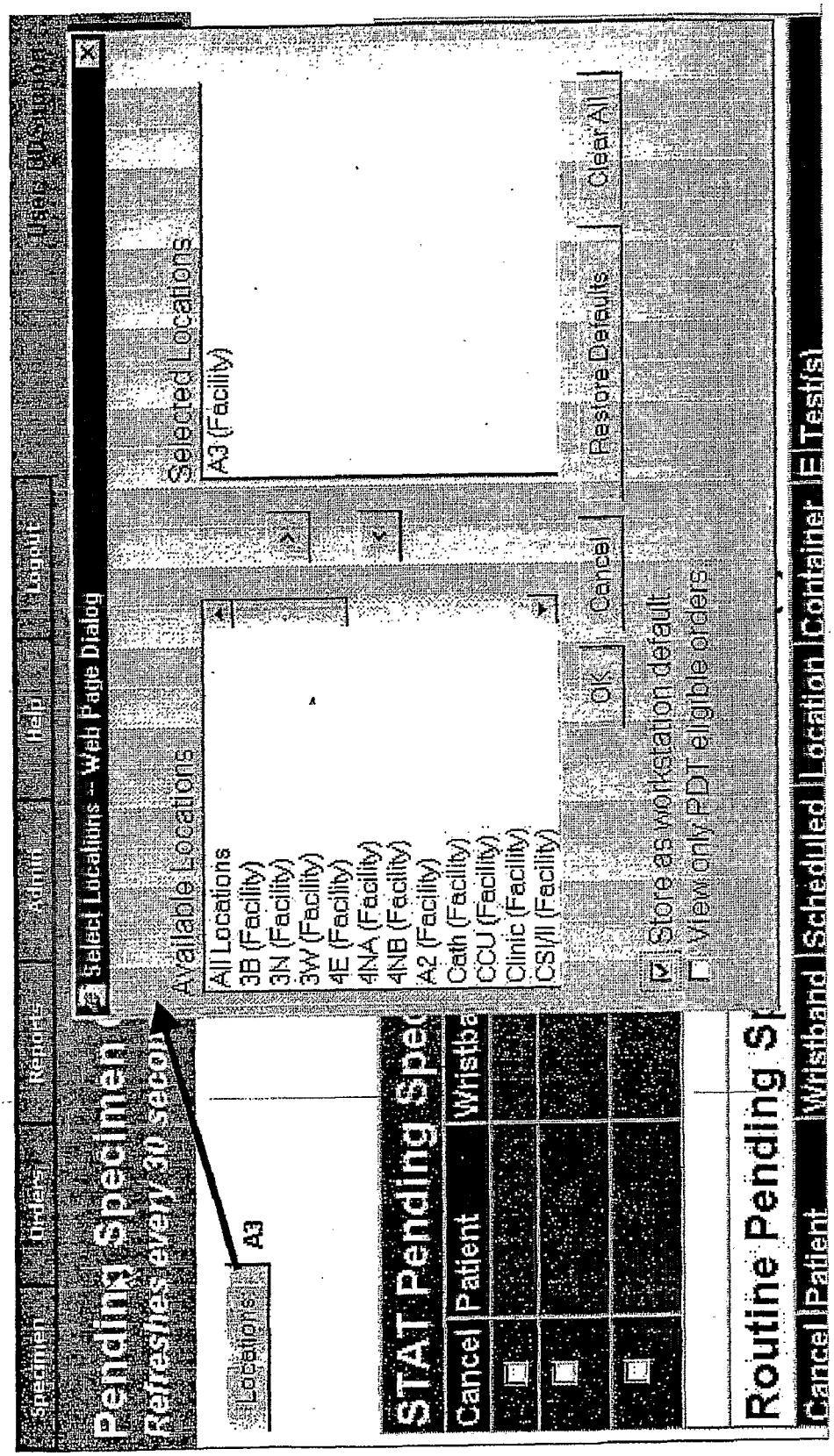

The UTC process is further illustrated in the flow chart depicted in FIG. 15. A physician writes an order or test in a patient's chart and the test is entered into the hospital computer system (e.g., LIS) (block 60). The test can then be provided from the LIS 24 to the server 20. The user of the PDT 22 to which the test is assigned (e.g., via a system administrator having a web interface to the server 20) uploads the PDT with information (e.g., from the LIS), as indicated in block 62. The user connects the PDT or handheld 22 to a portable printer and brings these devices and specimen collection supplies to the collection site (e.g., patient's bedside). As indicated in block 64, the user then correctly identifies the patient (e.g., by reading patient identification indicia), performs a collection, and scans the container to create a label to correspond the container to the collection event. If the container does not have a barcode, the user can select the "M" touchscreen button 47 (FIG. 7) on the handheld 22 to generate a manual label. The user then prints a specimen label for the collection container containing the collected specimen.

With continued reference to FIG. 15, if the order does not require more than one of the same type of container (block 66) and all of the required specimens are collected, the user sends the specimen(s) to the lab for processing and designates the test as complete using the handheld for reporting to the LIS (block 68). If the collection was unsuccessful, the order can be canceled. If a deviation event occurred and the collection was unsuccessful (block 70), and the order requires more than one of the same type of container, the user selects the UTC button 46 to properly disposition the uncollected specimen as UTC (block 72). The handheld then generates a warning message (block 74) that the other similar specimen containers will be given a UTC label (block 76) and/or a label for the collection bag or a communication signal will be sent to notify laboratory personnel that not all of the required containers are provided. The user then proceeds to collect the remaining samples needed to fulfill the order (block 78). In any event, the order is not incorrectly designated as complete or canceled.

A method to acknowledge and record an unexpected event or exception case in data collection is necessary for any error management system. It allows an accurate recording of an expected event that failed to occur, under certain circumstances, and assists with the determination of whether the unsatisfactory data collection event needs to be successfully repeated. In the hospital environment, when a patient blood collection order has been introduced to the LIS by a clinician, the order might have been assigned with identical samples to be collected for additional testing volume of patient sample.

However, if the additional identical sample could not be collected based on the situation, i.e., vein collapse, patient refusal to provide draw of blood, or other emergency, the system 10 provides the UTC feature to alert the LIS personnel of the error. This feature provides LIS staff proper communication and tracking of the erroneous order collection and allows them to decide if the sample is sufficiently important to require a future patient draw. Without the proper communication provided by the UTC feature of the present invention, LIS personnel might be required to reorder entire the specimen collection based on uncertainty of the information provided, causing analysis delays which leads to treatment delays.

The unexpected event error or exception case management communication feature is designed to provide information to laboratory personnel about the unavailability of an expected sample. As stated above, this information can be presented by a number of possible methods. One embodiment of the present invention employs means of outputting a print command to a printer upon selection of the UTC feature, that is, application of the UTC disposition to a particular repeated order via a button on the handheld. The printer can print a message label, or even barcode with information notifying the unexpected event (e.g., failure to collect). This information label can be part of or appended to an existing label, or can be completely separate from other collection order labels. This printed information can be sent to the laboratory with the successfully collected samples to be handled by proper agents. In addition, the UTC scenario can be communicated back to the LIS via a collection message, as well as the printed label, such as a wireless signal updating the LIS database and directly being sent to laboratory personnel.

Figure 11:
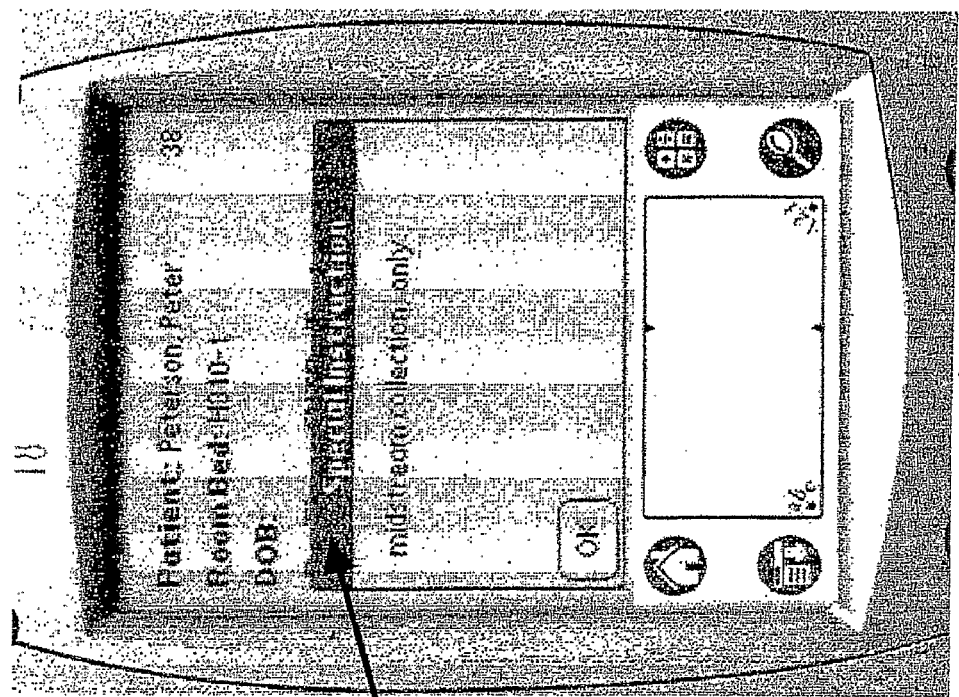
Figure 10:
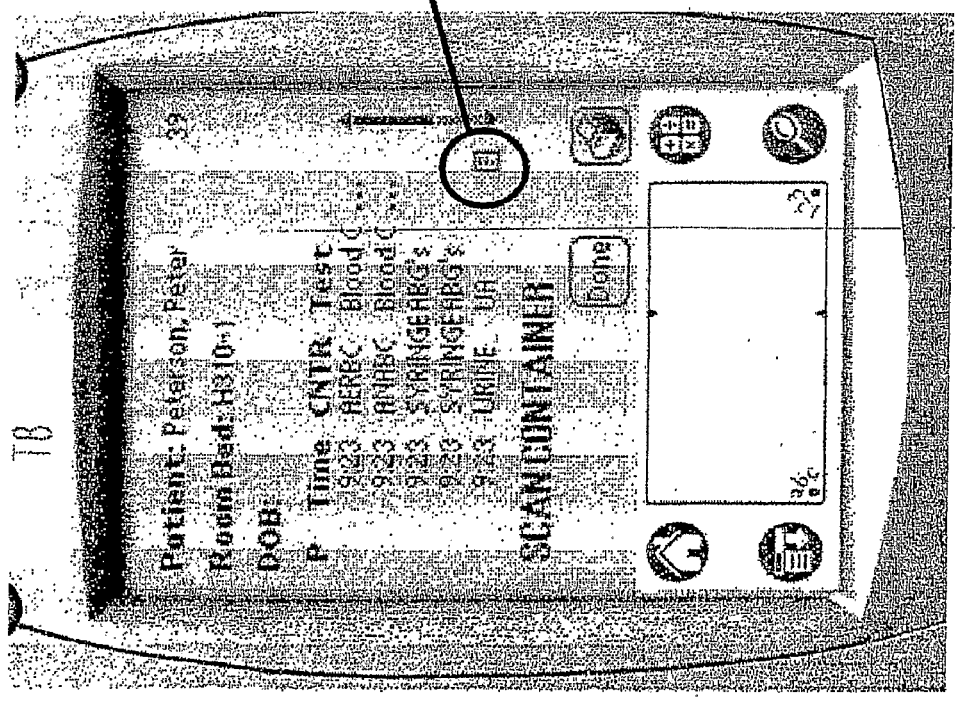
Figure 12:
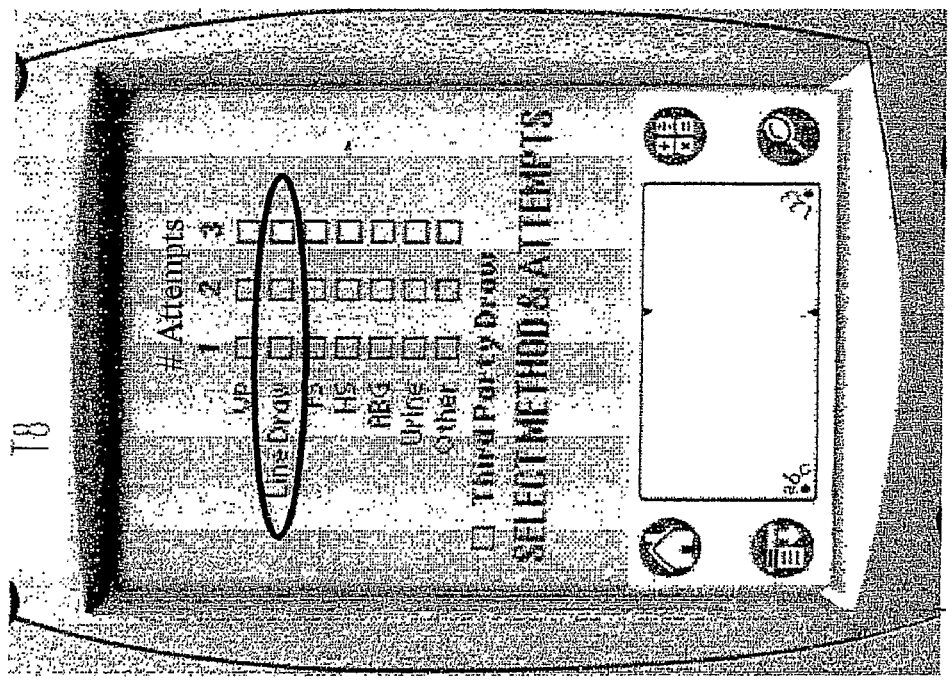
Figure 14:
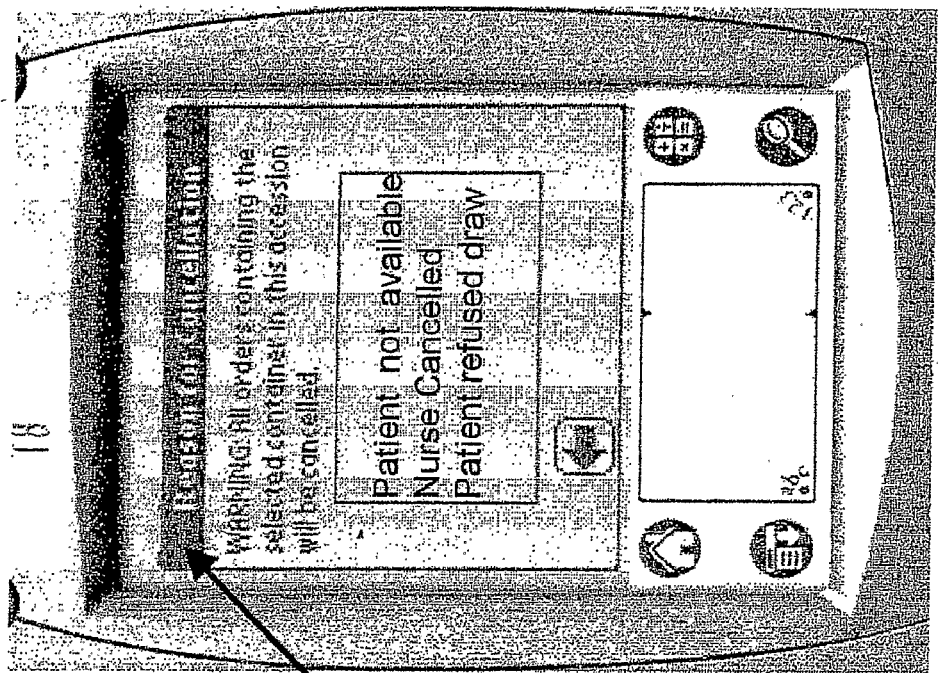
Figure 13:
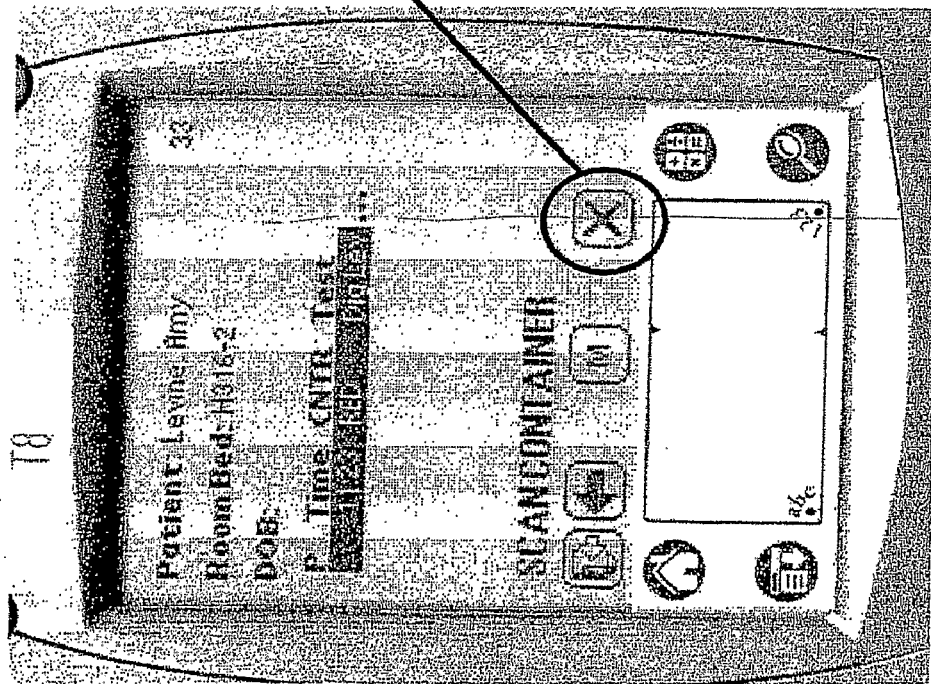

Other handheld screens include an icon (FIG. 10) to designate that an order has special instructions and a corresponding dialog box (FIG. 11). In addition, a workload screen (FIG. 12) and cancellation reason screens (FIGS. 13 and 14) are also provided. The workload screen (FIG. 12) allows for recording of the types of collections, including a line draw method, as well as the number of attempts to perform the collection to aide in managing workflow among medical staff. If the handheld user was unable to perform a collection, the workload screen (FIG. 12) allows designation of a third party draw if needed. The workload screen can be generated, for example, after a collection occurs and containers are scanned and labeled. The screen allows a handheld user to designate the type of collection (e.g., via venipuncture or VP, a line draw such as via a catheter, a finger stick or FS for filling a microcollection tube, a heel stick or HS, an arterial blood gas or ABG syringe, an open stream collection such as for urine or other), as well as collection via a person other than the person entering the collection data. Other handheld screens (not shown) can include, but are not limited to, patient lists sorted in accordance with selected criteria (e.g., priority of the collection such as a STAT, timed or regular draw, or by patient location such as by ward and/or room), order or draw procedural reminders or special handling instructions (e.g., a specific and predetermined order of draw) and order cancellation reason codes.

The system 10 is advantageous because it uses scanning of handheld user, patient and container IDs and correlates this information with specimen collections. In accordance with another aspect of the present invention, identifying labels can be printed from the system 10 to facilitate hospital business processes when those processes require a bar-coded label. The barcode label can be used for the facilitation of collection of specimens in the system 10 or for purposes unrelated to the system 10 and specimen collection. Typically, a patient has on him or herself a wristband identifier with unique indicia identifying who they are. This is typically presented in a barcoded format, but can also be presented through a RFID tag or by a displayed printed name. Also, typically portable handhelds and scanners are located in health facilities and include databases of patients that geographically align and relate to the portion of the health facility assigned to the handheld. Additionally handhelds remote to an LIS only are concerned with information about specimen collection orders that match those patients assigned to that portion of the health facility relevant to the handheld. Patient information not relevant to the handheld is ignored to avoid wasting memory storage on the handheld. Specimen collection using handhelds to facilitate tracking of specimens have included handhelds that can scan a patient, where the patient has an order pending from the LIS and the patient is in the handheld's database of relevant patients tracked in the handheld. However, sometimes in a healthcare facility a condition may exist where not all of the above conditions are met. These situations require different types of ID labels to be generated to assist with properly labeling collected specimens when, for example, there is no pending order or an order is repeated.

One such ID label is a Generic Temp ID label. An exemplary use for temp Ids is when a user needs to collect a specimen for which there is no pending order at the time of collection in the LIS. When an order may not be in the system and there is an immediate need to collect a specimen and connect the patient's information to that sample, the present invention also provides for the generation of a Demographic Temp ID label that includes some patient information and that can be used in this situation, as well as the Generic Temp ID label. The server 20 can get patient demographic information from a ADT feed or an LIS feed.

The Generic Temp ID label works as follows. A patient may be moved from one location of a hospital to another on a temporary or permanent basis. When the patient is moved from one location where he or she was appropriately assigned to a handheld to another location where he or she is not assigned to a handheld, information sent to the assigned handheld will not reach the users responsible for collecting his or her samples on his or her current floor, ward, location, etc. In this case, should a doctor or medical practitioner need to draw a blood sample not ordered by an LIS, he or she can activate a Generic Temp ID procedure. This procedure includes the following steps.

Figure 30:
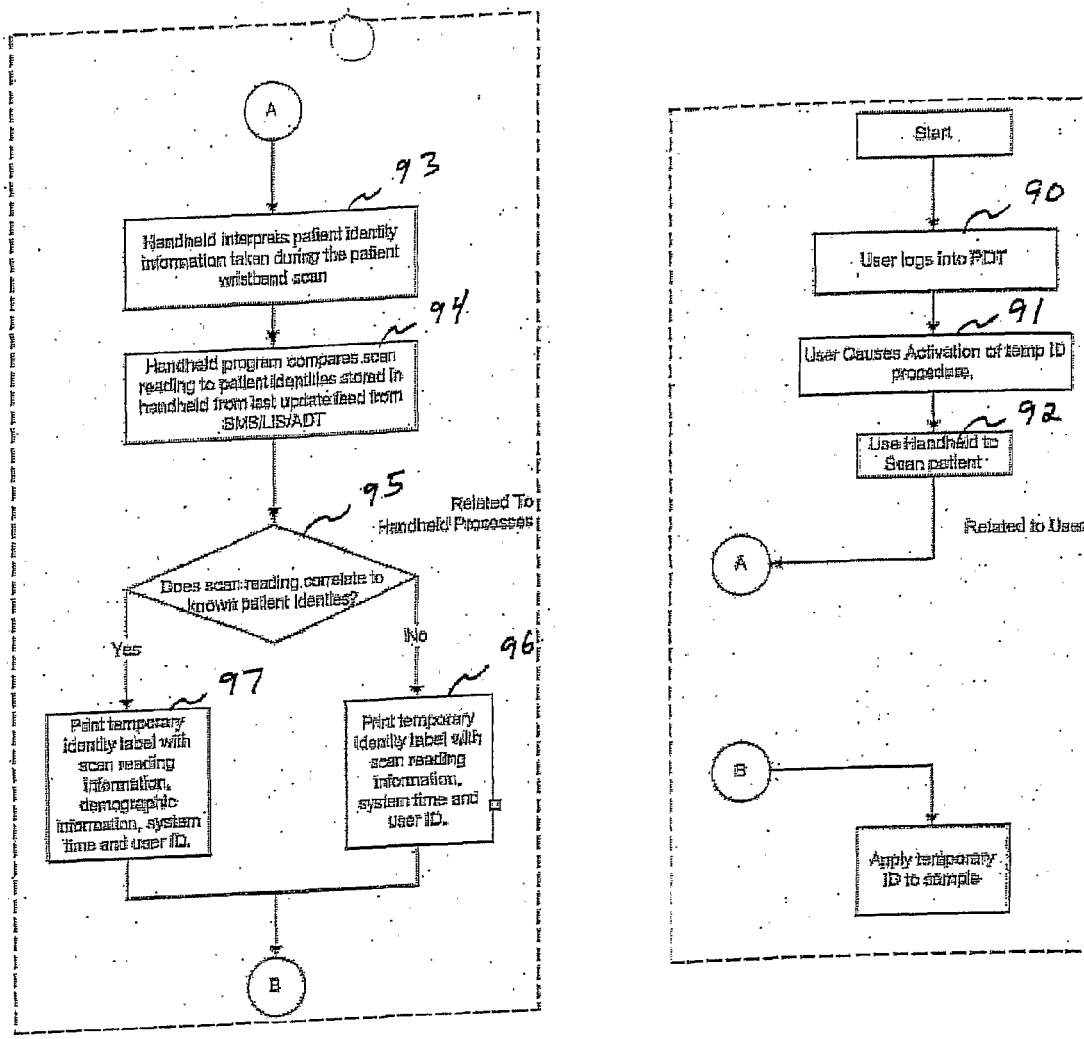
FIG. 30 is a flow chart depicting a sequence of operations for providing the Temp ID function of the present invention.

As outlined in FIG. 30, the user scans into the PDT (or handheld) 90, activates the temp ID procedure setup 91, scans the patient's identity information 92 such as a barcode on the patient's wristband, the handheld does not identify the patient as matching the list of patient's assigned to the handheld 93-95, and the handheld causes to be printed or generated a specimen container label at least including the patient's identity information 96. Additional information which may be included with the generated label may include time of collection, time or date stamp (such as but not limited to time/date of scan and time/date of procedure), or user ID.

The Demographic Temp ID label works as follows. A patient may be located in the appropriate area of a health facility where his or her information correlates with the patient lists on the handheld. However, sometimes a condition may exist where a specimen is required to be collected that has not been ordered through the LIS. In this case, should be a doctor or medical practitioner need to draw a blood sample not ordered by an LIS, he or she can activate a Demographic Temp ID procedure. This procedure includes the following steps.

As outlined in FIG. 30, the user scans into the PDT (or handheld) 90, activates the temp ID procedure setup 91, scans the patient's identity information 92 such as a barcode on the patient's wristband, the handheld identifies the patient as matching the list of patient's assigned to the handheld 93-95, and the handheld causes to be printed or generated a specimen container label at least including the patient's demographic information in addition to or in place of the patient's identity information 97. Additional information which may be included with the generated label may include time of collection, time or date stamp (such as but not limited to time/date of scan and time/date of procedure), or user ID.

In both the Generic Temp ID label and the Demographic Temp ID label, the label preferably includes an adhesive backing for placement and at least temporary fixation on a container. Additionally, the label may include a notch for alignment with a collection container such as that described in U.S. Pat. No. 6,428,640, herein incorporated by reference. Another exemplary use for a temp ID is when a nurse has difficulty collecting specimens from a patient and wants to notify an additional user by generating a label to facilitate the collection process. For example, when a nurse encounters a patient from whom it is difficult to collect a sample (e.g., due to a collapsed or difficult to find vein) and the nurse wants a more experienced phlebotomist to collect the sample, the nurse can print out a temp ID label. In response to these needs, the system 10 allows printing of the afore-mentioned two additional types of IDs. If the system 10 does not have record of the patient from either the ADT or LIS, then the Generic Temp ID can be printed. The content of the Generic Temp ID can be anything that the user (e.g., nurse) scanned, as well as the logged-in system user and system time. Typical usage would be to scan the wristband of a patient so that the label printer would print the wristband identifier in a bar-coded format, the system date, and the logged in system user.

When the system 10 does recognize the patient scanned because the patient's data is in the system 10 database due to a previous message from the ADT or LIS, then a Demographic Temp ID label is available to be printed with specific demographic information. In addition to collection purposes, both of these Temp ID labels can be used for pharmaceutical purposes, among other uses. Further, a two-dimensional barcode (e.g., a code with bars in a horizontal and vertical orientation) on a wristband can be used to obviate the need for the system 10 to have knowledge of a patient in order to print a Demographic. Temp ID. The two-dimensional code allows for scanning of only a portion of the coded pattern for recognition purposes. Thus, the two-dimensional code is useful when patient wristbands or barcodes on labels are only partially visible due to wear or other damage. The following steps explain how to use the PDT 22 to generate a label for a sample that has not been ordered in the LIS. A temporary ID label is placed on the patient sample until the order has been entered into the LIS.

1. Log into the PDT.
2. Select the location.
3. From the Patient List Screen, tap the Temp ID button.
4. A Temporary ID Label screen appears.
5. Scan the barcode on the patient's wristband.
6. The PDT prints out a temporary patient ID label.
7. Place the temporary ID label on the tube after collection of the sample.
8. Use the reprint function (tap the Printer icon) on the PDT if additional labels are needed.
9. Log out of the PDT and cradle it to receive new orders.
10. After the patient's order has been received by the BD.id System and downloaded to the PDT, log into the PDT.
11. Select the location.
12. At the Patient List Screen, scan the temporary ID label instead of scanning the patient's wristband.
13. The order list appears.
14. Tap on the order that corresponds to the tube with the temporary label (i.e. Scan the red top tube temporary label for the test that requires a red top tube).
15. Tap the Manual collect button (M) to generate a specimen label for that tube.
16. Place the specimen label over the temporary ID label.
17. Repeat the process if additional specimen labels are needed.
18. Complete the workload screen.
19. Log out of the PDT and re-cradle.

There are different types of tests (e.g., collections) that require different label sets, and clinical practices associated with collecting a specimen(s) and utilizing the label sets appropriately. In accordance with another embodiment of the present invention, the system 10 comprises an appropriately constructed and populated database and attendant logic rules for selecting and generating the appropriate label sets based on the test code received by the system, i.e., a patient identification system (PIS). The system 10 can also create and display appropriate workflow messages and alerts that are displayed proximally in time and location to the collection (e.g., via screens on a handheld 22) that guide the user to utilize the label sets appropriately and to take required or recommended actions in collection and preanalytical processing of the sample, e.g., tube handling, label application, conditions of transport, recording vital signs of patients, and signing documents. These messages can occur before, during, and after the collection process and can be configurable based on user input. The collection sets and messages can be based and generated on test/order codes or clinical information system codes (e.g., blood bank, laboratory, or microbiology). Examples include, but are not limited to pop-up alerts (e.g., "Alert doctor after collection" or "Specimen must be stored with ice") on handhelds 22 and unique subsets or combinations of labels (e.g., extra process direction labels for collection containers or bags to facilitate authorizations and workflow monitoring). This aspect of the present invention therefore represents an advantage over existing systems in which constant supervision is needed to ensure that messages are acknowledged and practices associated with the specific collection are performed. Unlike the present invention, label sets in existing systems are not generated at the collection location and time of collection must be brought to the collection site and are therefore disadvantageous.

The system 10 preferably comprises a web interface to the server 20 to facilitate system administration functions. FIGS. 16 through 26 illustrate exemplary screens generated by the web interface which can be displayed on an administrator workstation or other computing device connected to the system 10 (e.g., via the server 20) and having access to the web interface. Among other web pages, the web interface provides a pending specimen collection page (e.g., to view locations assigned to a workstation or handheld) and view data pages (e.g., to view canceled orders, removed orders, and orders by patient or transaction). The web interface provides security options for controlling the display of patient names and tests (e.g., based on user's security access level), for defining headers and priorities, as well as providing options or reason codes for canceling orders, among other functions. The web interface of the present invention provides administrative functions such as security functions (e.g., management of users such as by forcing password change and defining access rights for difference security roles), and selection of system parameters (e.g., parameters are grouped by PDT, pending specimen page, system and web interface parameters). Further, the web interface provides for variance tracking (e.g., variance groups and association of a variance with the actual collection event) and NCCLS order of draw for containers, both of which are described in more detail below.

The Pending Specimen Collections page (FIG. 16) shows the orders for the patients in the selected location(s). The orders are grouped by priority within priority group and sorted by location, then bed, then scheduled date/time, then container. This page can open as the default page for the BD.id System web site.

Security

A system parameter allows the site to control if a user must log in prior to displaying this page. To safeguard patient confidentiality, there are two system parameters that control the number of characters to be displayed for patient names and test orders. This partial display of patient data prevents the "casual observer" from acquiring patient order information. When the system automatically refreshes the list, the system displays a "partial" format for the patient names and test names based on user settings. When a user clicks on the REFRESH NOW link, the system displays the entire patient name and test orders.

Locations

The Locations button allows the user to select locations to be displayed. This window allows the user with the appropriate access rights to set the default locations for the workstation. However, the user may edit the locations to view orders from other locations without changing the default locations. If a user has access rights for "Specify Location(s) for workstation" the window for Locations has two options available:

| Option | Definition |
| --- | --- |
| Store as workstation default | When this box is checked, the selected locations are stored as the default locations for the workstation. |
| View only PDT eligible orders | When this box is checked, only orders that qualify to be sent to the PDT are displayed on the Pending Specimen Collections page.<br>If this box is not checked, all orders for the selected locations are displayed. An additional column "E" shows a checkmark for those orders that are eligible to be sent to the PDT. |

To Change the Selected Location(s):
1. Click on the Locations button. The Select Locations pop-up window is displayed.
2. Select the location from the Available Locations list by clicking the location and then click the right arrow button to add the location to the Selected Locations list.
3. After selecting the locations, click the OK button. This will display the Pending Specimen Collections for the locations selected.
   Note: Click the Cancel button to start over. To remove a location from the selected list, click on it and then click on the left arrow button. To remove all items in the selected list, click the Clear All button. Select the Restore Defaults button to select the locations that were used during the last web page session.

Canceling Orders

The first column header (Cancel) on the list contains a checkbox for each order on a specific container. The orders for a container are canceled by checking this box and pressing the Cancel button on the bottom of the page or pressing the ENTER key. The system requires the user to login to ensure the user has access rights for this function. The Cancelled Orders page displays the selected orders. A cancel reason must be selected before the cancellation can be entered. The canceled order data may be sent back to the LIS if the interface supports this feature.

Changing the Sort Order

The Pending Specimen Collections page allows you to sort in ascending or descending order based on Patient, Wristband, Schedule, Location, and Container for all priority groups.

To sort in an ascending order, select the Patient, Wristband, Schedule, Location or Container header and click. An "A" on top of a "Z" with a down arrow indicates an ascending sort method.

To sort in descending order, click the header with the "A" and "Z". A "Z" on top of an "A" with a down arrow indicates a descending sort method.

To sort using the default parameters (by priority and room/bed within location within collection date), click the Default Sort Order button located in the upper right corner of the page.

Eligible (E) Column

The Pending Specimen Collections page displays an "E" column under each priority header when all orders have been defined to appear on this page. The "E" column indicates orders that are Eligible for download to the PDT. In most instances the orders are download to the PDT approximately 180 minutes before the specimen collection is due.

Viewing the Pending Specimen Collection List
1. Open the BD shortcut on your desktop. The Pending Specimen Collections page is displayed. The list may also be displayed by selecting the Pending Specimen Collections option from the Specimens menu.
2. Enter your Username and Password if required.
3. Click the Locations button. The Select Locations pop-up window is displayed.
4. Select the location from the Available Locations list by clicking the location and then click the right arrow button to add the location to the Selected Locations list.
   Note: To remove a location from the selected list, click on it and then click on the left arrow button. To remove all items in the selected list, click the Clear All button. Click the Restore Defaults button to select the locations that were used during the last web page session. Click the Cancel button to start over.
5. When you have finished selecting the locations, click the OK button. The system displays the Pending Specimen Collections for the locations selected.
6. To view the full patient names and Test data on the Pending Specimen Collection, click the Refresh Now link. A user login may be required.

Figure 21:
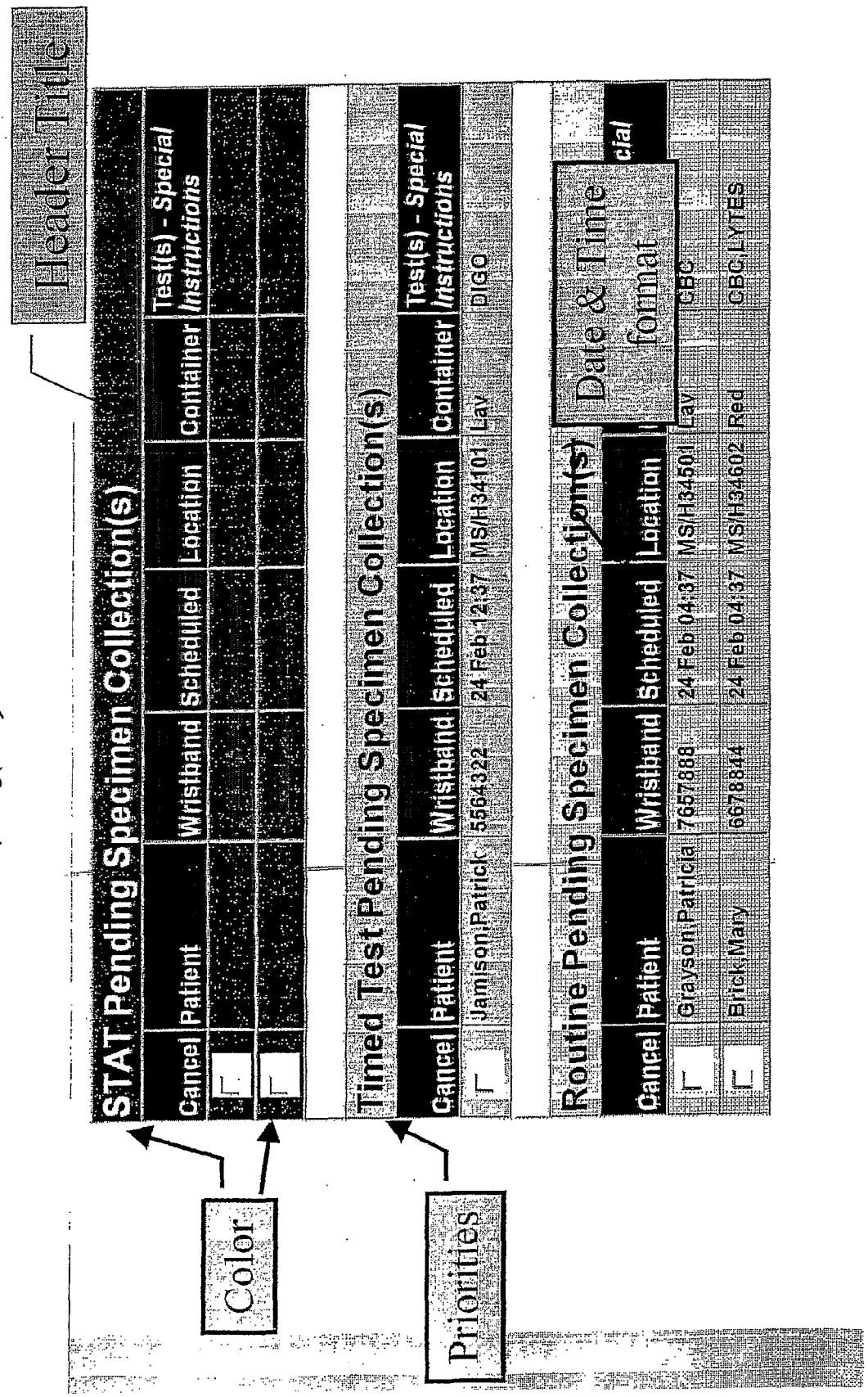
Figure 23:
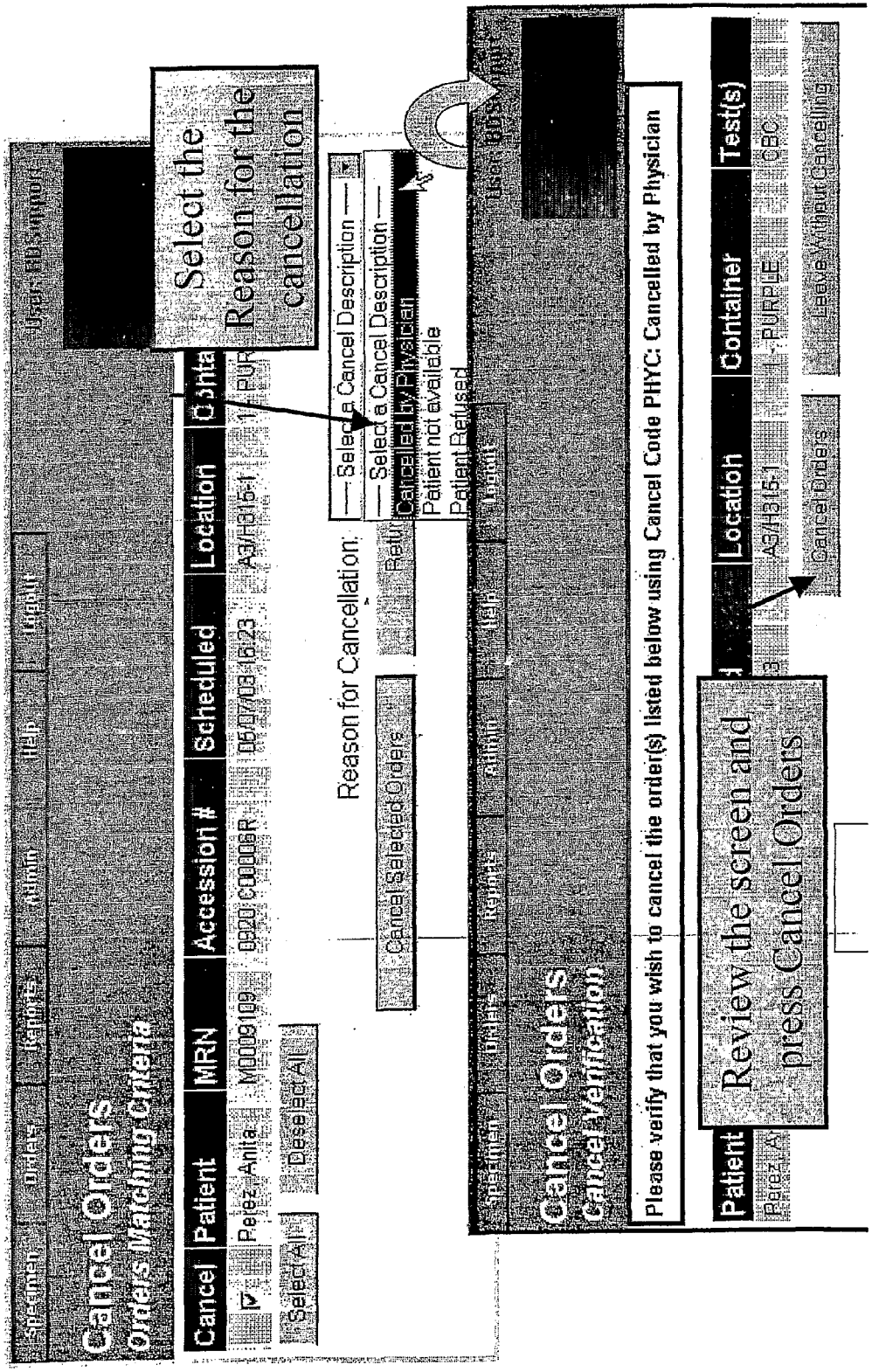
Figure 24:
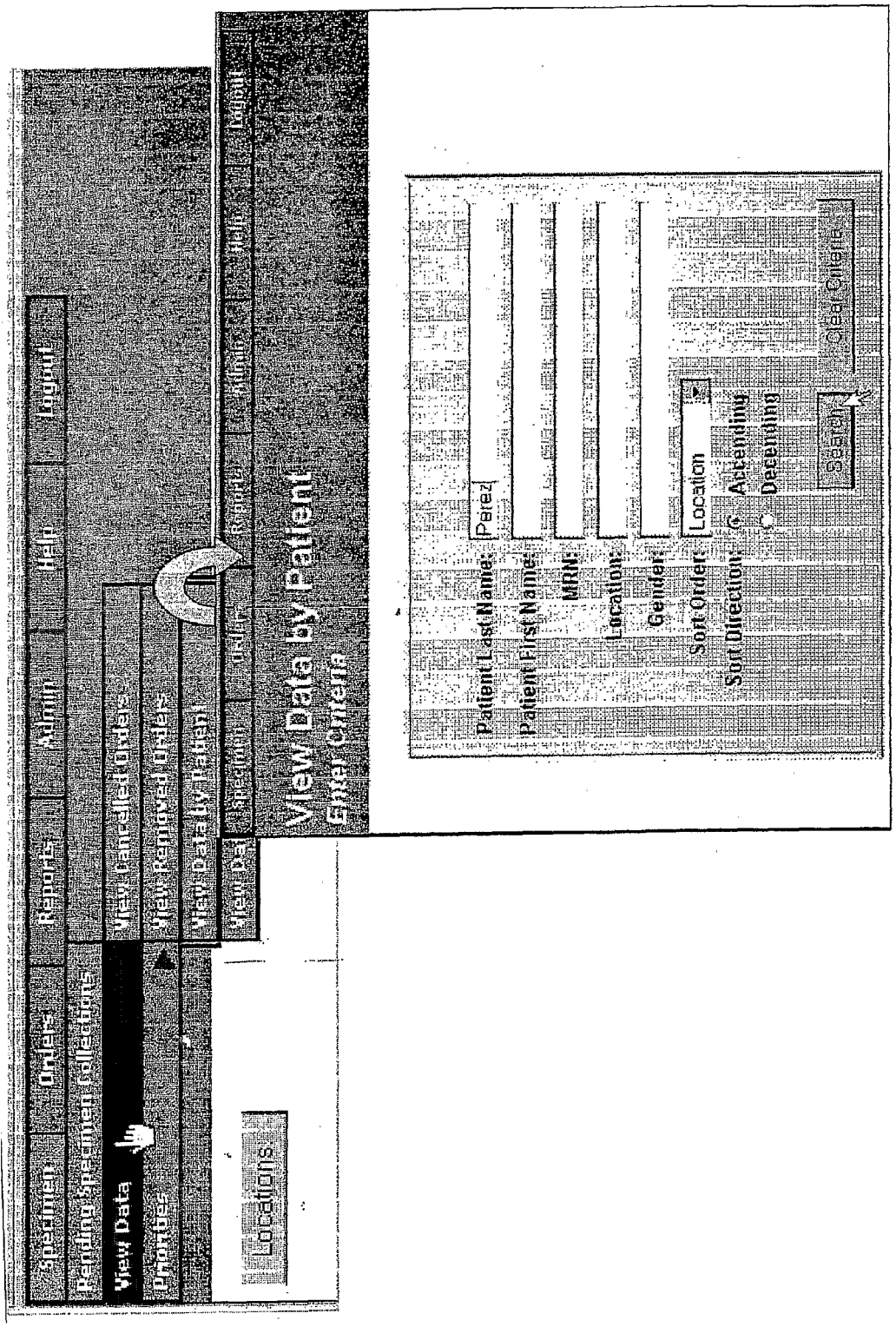
Figure 25:
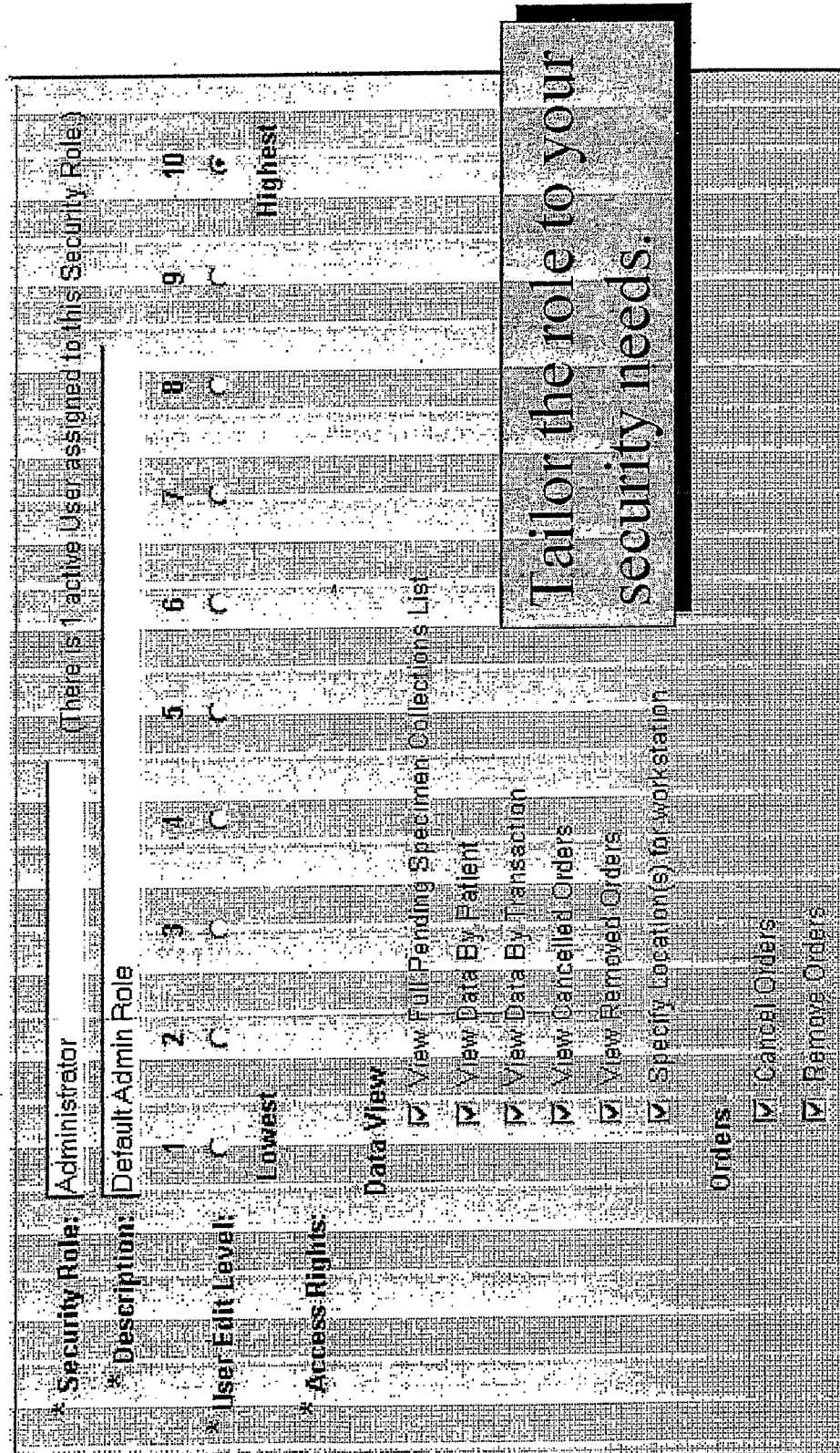
Figure 2U:
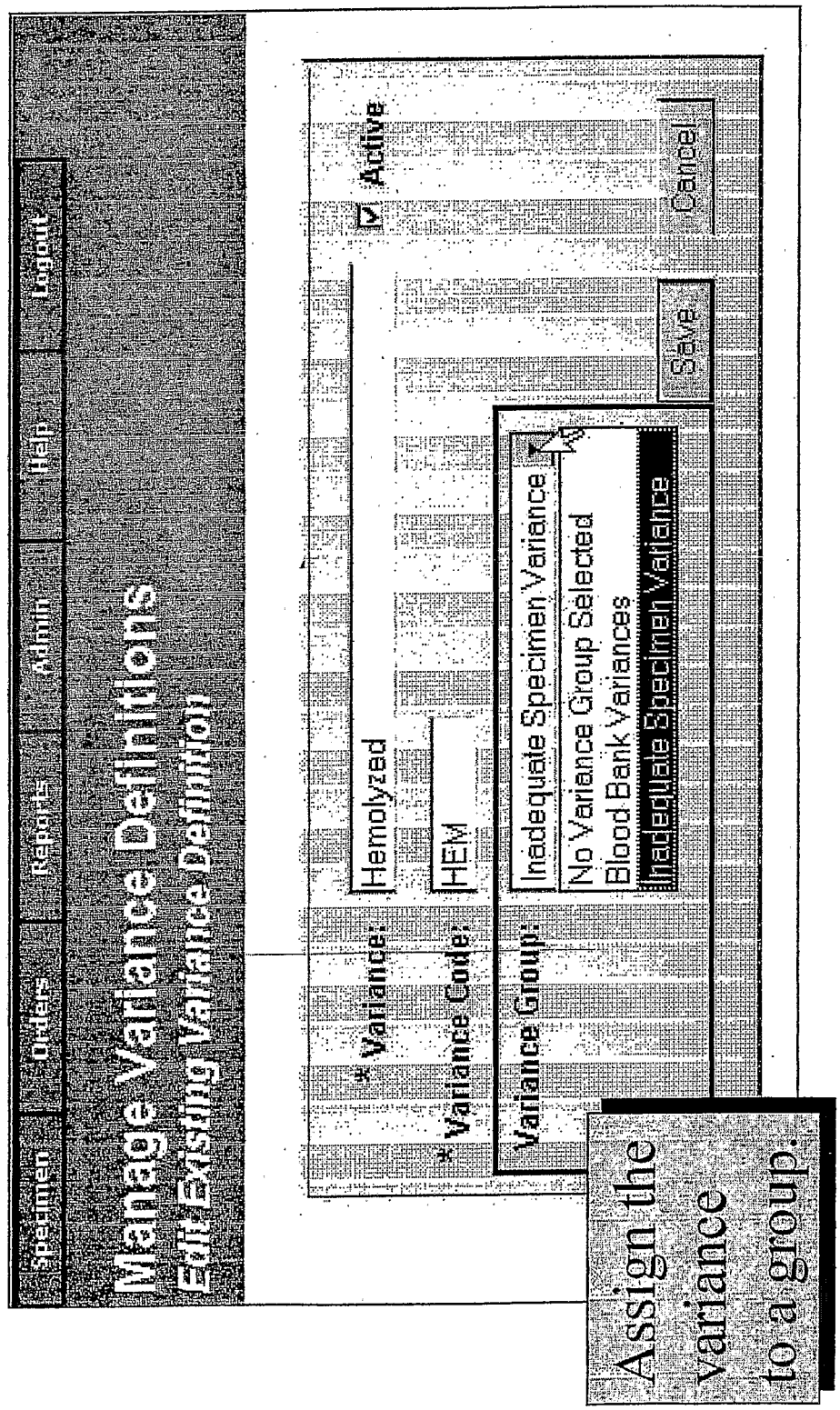

The Header definitions for the Pending Specimen Collections page may be defined and edited by the user. With reference to FIG. 21, the definitions include the priority codes assigned to each header, the sorting of the priority codes within a header and the colors to be applied to each header. The Pending Specimen Collection page groups pending orders by priority code. The user associates each priority code to a user defined group header, e.g., STAT, Timed, Routine, etc. If a priority code is used for Timed Test(s), refer to the system parameter for defining the Warning Time Window that alerts the user that a Timed Test is scheduled and has not been collected.

Managing Priority Groups
The Priority Groups are defined with their headers and colors.

| Field | Description |
|---|---|
| Priority Group Name | Enter the name for this group of orders. |
| Priority Header Label | Enter the text for the priority header that prints as a second line under the group name. This text will only appear if the box to Display Priorities is selected. |
| Display Priorities | Check this box if the priority codes assigned to this header are to display with the Priority Header Label. |
| Sort Order | Enter a value from 0-255 to determine the sorting of this header in relation to the other group headers. |
| Display Special Instructions | Check this box if Special Instructions are to be displayed for this group. |
| Group Header Colors | Select the background color and the text color for the header. |
| Group Table Colors | Select the background color and the text color for the table. |

Managing Priorities
The Priority Codes are entered and associated with a Priority Group.

| Field | Description |
|---|---|
| Priority | Enter a priority code. |
| LIS Priority | Enter the LIS priority code. |
| PDT Short Priority | Enter the abbreviated form of the code to be displayed on the PDT. For example, "S" for STAT. |
| Sort Order within Group | Enter a value from 0-255 to determine the sorting of this priority within the group. |
| Timed Test | Check this box if this priority is used for a Timed Test. |
| Priority Group | Select the Priority Group to display orders having this priority code. |

Priority Groups are Defined Before Priority Codes.
To Enter a New Priority Group:
1. From the Specimen menu, select the sub-option Manage Priority Groups under Priorities.
2. Enter your Username and Password.
3. The View Existing Priority Groups page is displayed if you have access rights.
4. Select the Add New button. The Add New Priority Group page is displayed.
5. Enter the information in the fields.
6. To save, click Save. To ignore any changes, click the Cancel button.
To Edit a Priority Group:
1. From the Specimen menu, select the sub-option Manage Priority Group under Priorities.
2. Enter your Username and Password.
3. The View Existing Priority Groups page is displayed if you have access rights.
4. Click on the Edit icon. The Edit Existing Priority Group page is displayed.
5. Modify the fields.
6. Click the check box next to Display Priorities to display the priority codes assigned to this Priority Group with the priority header label.
7. To save changes, click Save. To ignore, click Cancel.

To Enter a New Priority Code:
1. From the Specimen menu, select the sub-option Manage Priorities under Priorities.
2. Enter your Username and Password.
3. The View Existing Priorities page is displayed if you have access rights.
4. Select the Add New button. The Add New Priorities page is displayed.
5. Enter the information in the fields.
6. To save, click Save. To ignore any changes, click the Cancel button.
To Edit a Priority Code:
1. From the Specimen menu, select the sub-option Manage Priorities under Priorities.
2. Enter your Username and Password.
3. The View Existing Priorities page is displayed if you have access rights.
4. Click on the Edit icon. The Edit Existing Priorities page is displayed.
5. Modify the fields.
6. Click the check box next to Active to remove the check and inactivate this Priority.
7. To save changes, click Save. To ignore, click Cancel.

The System Parameters allow the user to tailor the system to their environment. Key features of the system can be activated or disabled based on the internal procedures of each client site. The parameters are grouped according to the system module affected: PDT Parameters, Pending Specimen Collections Page, System Parameters, and Web Parameters.

As stated above, another advantage of the system 10 is its ability to provide variance tracking that is linked to an actual collection event or instance in accordance with another embodiment of the present invention. An order starts in the LIS and is delivered to the server 20, for example, and is then delivered to the end user for collection. Upon collection, the specimen and container are delivered to the laboratory where it is reviewed. If the collection or specimen is determined to be in error by the laboratory, the system is capable of storing and reporting the collection error. The error is then entered into the system 10 (e.g., via the server 20), which links the error to the specific collection, which allows long term reporting of who, when and where errors in specimen collection have occurred. The information is reported back to the users via textual and/or graphical reports via the web interface or remote computing device.

In an embodiment of the present invention, the user enters the variance information into the system 10 using the web interface and lists the variance that occurred and the person that reported the variance(s), and selects the collection that created the collection specimen that was flawed. The user then can generate reports that include information pertaining to the variances including the identify of the user, the PCT unit, the specimen collected, the time of the collection, and the collection method used in generating the specimen. It is to be understood that the term "collection" refers to whatever list of samples intended to be collected during the collection process. In other words, one or many blood collection tubes may signify one collection in connection with variance tracking.

The management of variances via the web interface will now be described. A variance is defined for each type of error incurred during specimen collection. The variance group (FIG. 26) allows the user to assign each variance to a category in order to view statistics by groups rather than viewing each individual variance. Examples of Variance Groups are: Analytical Errors (hemolysis, short draws, incorrect container), Specimen Identification Errors, Blood Bank Specimen Errors. The group names are defined first in order to assign the individual variances to a group.

The variance form contains the following fields:

| Field | Definition |
| --- | --- |
| Variance Code | Enter a code for the variance. (e.g., CLTD for Clotted). |
| Variance Group | Select the group associated with the code. |
| Active | When editing a code this option appears. To inactivate a code, click on the box to remove the check. |

Entering a Collection Variance

To enter a collection variance, a selection form is displayed to find the patient's specimen associated with the variance. After finding the specimen, click the Append Variance icon. The system displays transaction data for the specimen and allows you to check the appropriate variance and enter the name of the person who reported the variance.

Collection Variance Search

The Collection Variance search is used to find the patient specimen to enter variances that are manually recorded on the laboratory variance log sheets. The data for the patient specimen is displayed and allows a variance to be associated with the specimen and enter the user who reported the variance.

1. From the Admin menu, select the sub-option Collection Variances under Manage Variances.
2. Enter your Username and Password.
3. The Collection Variance Enter Criteria page is displayed if you have access rights.
4. Enter criteria in the selection form fields and click Search to find the patients/specimens matching the criteria entered.
   Note: None of the fields are required. Clicking Search with no selection criteria will display a list of all patients/specimens that qualify.
5. The Collections Matching Criteria page is displayed.
6. Click the Append Variance icon next to the patient information you want to select. The Append Variance page is displayed with the patient/specimen information.
7. Click the check box next to the variance to associate the variance with this specimen.
8. Select a user from the User in the system drop down box or type a user name in the User NOT in the system box for the user who reported the variance.
9. Click Save to save the variance information or click Cancel to ignore the information and return to the Collections Matching Criteria page.

Edit Variance Definitions

A variance is defined for each type of error incurred during specimen collection. To add a new variance:

1. From the Admin menu, select the sub-option Edit Variance Definitions under Manage Variances.
2. Enter your Username and Password.
3. The View Existing Variance Definitions page is displayed if you have access rights.
4. Click Add New. The Add New Variance Definition page is displayed.
5. Enter data in the Variance field.
6. Enter data in the Variance Code field.
7. Make a selection from the Variance Group drop down list.
   Note: Variance Groups must be defined first before assigning the individual variance to a group.
8. Click Save or Save & Add Another to save the variance information. To ignore, click Cancel.

To Edit a Variance:

1. From the Admin menu, select the sub-option Edit Variance Definitions under Manage Variances.
2. Enter your Username and Password.
3. The View Existing Variance Definitions page is displayed if you have access rights.
4. Click the Edit Variance (pencil) icon next to the variance to be edited. The Edit Existing Variance Definition page is displayed.
5. Modify the fields for this variance.
6. Click the check box next to Active to remove the check and inactivate this variance.
7. To save changes, click Save. To ignore, click Cancel.

Edit Variance Groups

Variance Groups allow assignment of individual variances to categories for viewing statistics. For example, a variance group for Analytical Errors may include these individual variances: Hemolysis, Short Draws, Incorrect Container, Specimen Identification Errors, etc. Variance Groups must be defined first before assigning individual variances to a group.

To Add a New Variance Group:

1. From the Admin menu, select the sub-option Edit Variance Groups under Manage Variances.
2. Enter your Username and Password.
3. The View Existing Variance Groups page is displayed if you have access rights.
4. Click Add New. The Add New Variance Group page is displayed.
5. Enter data in the Variance Group field.
6. Enter data in the Short Name field.
7. Click Save or Save & Add Another to save the information. To ignore, click Cancel.

To Edit a Variance Group:

1. From the Admin menu, select the sub-option Edit Variance Groups under Manage Variances.
2. Enter your Username and Password.
3. The View Existing Variance Groups page is displayed if you have access rights.
4. Click the Edit Variance Group (pencil) icon next to the variance group to be edited. The Edit Existing Variance Group page is displayed.
5. Modify the fields for this variance group.
6. To save changes, click Save. To ignore, click Cancel. Click Delete to remove the variance group.

In accordance with another aspect of the present invention, means are provided to allow the system 10 to assign collections based on some criteria derived from information contained in the Clinical Information System (CIS), provided externally, or as defined within the system to a set of defined health care providers, a specific individual, or to a specific device or set of devices. In one example, this aspect of the system 10 can be used to take information from the CIS and target an order to be collected by a specific category of user, such as a nurse or a phlebotomist. In another example, the system 10 can take information from the CIS and target an order for a set of devices (e.g., handhelds 22) specifically configured for STAT orders. In another example, the system 10 can take information from the CIS and associate an order to a specific user (scanning of user would drive the set of orders displayed for that user).

The order of draw aspect of the present invention will now be described in conjunction with FIGS. 27, 28 and 29. In the hospital and laboratory environment, blood samples are frequently ordered by doctors to be collected and sent to the lab for blood analysis. The samples of blood are typically collected into evacuated collection containers or tubes using some sort of venipuncture procedure. Such procedures include, but are not limited to, using venipuncture devices such as wingsets, double-ended straight needles, catheter ports, etc. All of these devices are used with a non-patient needle which allows for a blood collection tube to establish fluid communication between the patient's vein and the evacuated chamber inside the tube.

Blood collection tubes come in many varieties and have different additives, fill volumes, and other characteristics resulting in a myriad of containers to be chosen from when a specific test is ordered. For example, some tubes accelerate clotting of blood while others postpone or prevent clotting of blood. Other tubes provide a density gradient so that blood collection tubes can be centrifuged, causing their cellular components to be separated by specific gravity.

Typically a nurse or phlebotomist will receive an order to collect certain tubes based on the type of test that was ordered by the laboratory and/or doctor. Depending on the hospital procedure that communicates to the nurse or phlebotomist what tubes are needed, there can exist a lack of information guiding the phlebotomist in which order to collect the containers or tubes ordered. This information is important because certain tube additives may contaminate the specimen in a subsequent tube if the additive on the previous tube contaminates the blood collection needle used to deposit sample into the subsequent tube. In general, the order of draw is designed to prevent cross contamination that can result in erroneous lab results. A specimen is the biological representation of a patient and therefore if the phlebotomist doesn't use the proper order of draw, the biological make up of that specimen could be compromised and no longer is a true representation of the patient. Something as seemingly simple and undetectable as changing the order of draw during the procedure can create a change in the representation of that specimen. Care and consideration of the proper order of draw is significant to good patient care, and therefore a demonstrated need for the present invention.

To avoid the contamination of additives between tubes, a guideline has been set by a widely recognized standards organization to avoid this potential problem. The guideline provides a recommended order in which the tubes should be collected. One generally recognized standards organizations is the National Committee for Clinical Laboratory Standards (NCCLS). Hospitals and laboratories typically display throughout their institutions in pamphlets or posters the recommended NCCLS suggested order, thereby assisting the nurse or phlebotomist in determining what order to draw tubes when multiple tubes are to be drawn for a certain test.

When a suggested list is not readily available, the nurse or phlebotomist relies on his or her experience or memory to chose the order he or she thinks is correct. The flexibility a nurse or phlebotomist has to deviate from the preferred order of collection allows for some collections to be collected in an erroneous manner, thereby subjecting certain tubes to the possibility of incorrect laboratory results. In order to reduce and hopefully prevent the possibility for erroneous collections, an embodiment of the present invention utilizes a handheld specimen order display to reduce or eliminate erroneous collections.

Such embodiment includes the use of an algorithm to communicate to a handheld device the correct order of containers to be drawn. The invention can be implemented in an LIS, in a server that bridges the LIS and the handheld, or to the handheld directly. In some embodiments, the LIS can directly communicate to at least one and usually a plurality of remote handheld devices, those specimen containers that should be collected from a patient assigned a pending test. When referring to direct communication, the LIS can output a priority list of containers that is displayed on the handheld by a sequencing feature in either a handheld resident program or an algorithm in the LIS. When referring to indirect communication, the LIS can send to intermediate system information that the intermediate system translates into the proper sequence acceptable and displayable on the handheld. The intermediate system could be, for example, a server in communication with the LIS. Other intermediate systems are contemplated and possible to use, as long as the intermediate system has algorithms to translate the containers into a preferred sequence that is displayed on the handheld so that an acceptable order of draw is communicated to the user.

Typically, the LIS has defined within it a database of mnemonics for each collection container used to collect patient specimens. For example, the mnemonic RED6 might be equivalent to a serum (red top) tube that has a 6 ml draw volume. Mnemonics are used to communicate to the nurse or phlebotomist which tube or container should be used to carry out a sample collection procedure. Nmeunomics are typically defined by the laboratory or hospital and correlated to a specific tube or container such as by a tube or container catalog number. In general, each container or tube has only one mnemonic as well as only one associated catalog number.

By constructing an appropriately populated database and logic rules from order codes and container mnemonics resident in a CIS (computer information system, more specifically a hospital information system, and even more specifically a laboratory information system), physical products needed for specimen collection are displayed in the appropriate order of collection based on a recommended standard, e.g., NCCLS. A remote computing device is preferably used to display the information to a care provider.

In one embodiment of the present invention, a server receives orders from a CIS containing order codes and container mnemonics. Container mnemonics indirectly determine what physical products (tubes or containers) that can be used in the collection of the specimen. The server presents the order of those mnemonics to the user collecting the biological fluid samples from a patient in a correct sequence such that the physical products are collected in accordance with NCCLS recommended order of collection.

Specifically, the present invention (a server 20 such as the afore-mentioned BD.id system) provides a means to map physical products to container mnemonics thereby associating a NCCLS sort order with the container mnemonic. A sort value is generated for all types of containers identified in the NCCSL sort order. A high priority NCCLS sort value means that the container or tube associated with the mnemonic is presented to the phlebotomist or nurse in a manner to indicate such. In the case where no physical product is associated with a container mnemonic, the lowest priority NCCLS collection sort value is applied to the mnemonic. On the remote computing device, the orders are then displayed using the NCCLS sorting value associated with each container mnemonic. Therefore, the user of the remote computing device will know exactly which order should be used and in what sequence.

In one embodiment, the display on the handheld can display the orders in order of priority (commercial embodiment). In another embodiment, the display on the handheld can display the orders in a sequence that is different than the order of priority, but could additionally display a priority identifier so that the user would know in which order to draw the samples. For example, a priority ranking for each container could be displayed adjacent to the container so that even if the order of containers displayed is not in an order that correlates with the priory ranking determined by the sort value generator, the user still knows which containers to collect first.

The desired order for collecting specimens is defined by a standard acceptable to the laboratory. The laboratory LIS may have within it a NCCLS standard, a standard derived by another third party, a standard developed by the institution or hospital, or a combination thereof. Preferably, the NCCLS standard is used to determine proper tube draw order for collecting containers of a biological fluid specimen, such as blood. The NCCLS standard might be dependent on which type of collection is performed, and therefore it is contemplated that the invention can acknowledge the difference if what type of collection is to be performed and make adjustments as needed. (Types of collection include evacuated tube use for venipuncture; syringe draws, or capillary draws). The most common type of collection performed in hospitals is through the use of evacuated blood collection tubes. Other forms of collections include but are not limited to capillary draws, and syringe draws. The order for drawing blood collection tubes might vary when compared to the order for capillary or syringe draws. One aspect of the present invention is to provide algorithms that differentiate which mnemonic is associated with the type of draw, and then to select the appropriate NCCLS standard applicable to that type of collection procedures.

Below is a representation of NCCLS standard H3-A3 which recommends that tubes be collected in the following order of draw:
1) blood culture tube or bottle (aerobic and anaerobic)
2) plain serum tubes (e.g., a red stopper-glass non-additive or plastic clot activator)
3) * coagulation tubes (e.g., sodium citrate tube additive with a blue stopper)
4) ** non-citrate additive tubes, herein referred to as additive tubes (e.g., with a green, lavender, or gray stopper, or other additive tube). Examples include sodium heparin, lithium heparin, EDTA, Oxalate fluoride, etc.

* When a black-topped buffered sodium citrate tube has been requested, it should be filled after the plain serum tubes but before the additive tubes, therefore, before or after the coagulation tubes. Black-topped buffered sodium citrate tubes are used for sedimentation rates.

** When multiple additive tubes are requested, their sequence of draw within the along with the coagulation tubes prior to the non-citrate additive tubes. When several different non-citrate additive tubes are requested, their order within the broader group is also important. For example, the order for additive tubes are as follows:
1. Heparin-containing (green stopper) tube.
2. $K_2$ EDTA or $K_3$ EDTA containing (lavender stopper) tubes.
3. Clot activator (gray and yellow stopper) tube (CAT) containing thrombin.
4. Gel or mechanical separator (gold stopper) tubes (i.e., serum separator tube, or SST).

The order in which multiple tubes are collected can affect the results of a test. The "order of draw" is a set of guidelines prepared by the National Committee for Clinical Laboratory Standards (NCCLS) to minimize problems associated with multiple tube collections. With the exception of blood cultures or other tests that require special techniques to minimize the possibility of microbial contamination, the order in which the evacuated tubes are used is different from the order in which tubes are filled when using a syringe to draw the blood. This order is designed to reduce interference in specimen testing caused by inadvertently mixing additives between tubes. This can occur when blood in a tube that contains an additive makes contact with the needle that punctures the tube's rubber top. Blood remaining within the needle may be transferred to the next tube, contaminating that tube, thus affecting test results on that specimen. Each laboratory may have their own Order Of Draw Policy.

| SAMPLE ORDER OF DRAW | COLOR OF STOPPER | COMMENTS THAT MAY BE DISPLAYED ON THE HANDHELD IN ADDITION TO THE RECOMMENDED SEQUENCE. |
|---|---|---|
| 1 | Blood Culture Collection Bottle | When a culture is ordered along with any other blood work, the blood cultures MUST be drawn first. |
| 2 | Plain Red Serum Tubes | Contains no additive in glass tubes (clot activator additive in plastic serum tubes). Do not mix or invert. Used for serum test(s), which cannot be collected in SST tubes. |
| 3 | Light Blue | Referred to as Blue Top tube. Contains Sodium Citrate anticoagulant. This tube is used mainly in coagulation studies. |
| 4 | (SST) Red/Gray or Gold Plastic Cap | Throughout this Guide, we refer to this as SST. Most commonly used tube where serum is required. Contains a gel separator and clot activator. |
| 5 | Royal Blue (Green Band on Label) | Contains Sodium Heparin anticoagulant This tube is required for collection of trace elements. |
| 6 | Dark Green | Contains Sodium Heparin anticoagulant. |
| 7 | (PST) Light Green (mint) Green/grey | Contains Lithium Heparin anticoagulant as well as a gel separator |
| 8 | Lavender | Contains EDTA anticoagulant. |
| 9 | Pale Yellow (ACDA) | Contains Acid Citrate Dextrose Solution 'A' and is used primarily for Flow Cytometry testing. |
| 10 | Pale Yellow (ACDB) | Contains Acid Citrate Dextrose Solution 'B' and is used primarily for Bone Marrow Donor Registry |

-continued

| SAMPLE ORDER OF DRAW | COLOR OF STOPPER | COMMENTS THAT MAY BE DISPLAYED ON THE HANDHELD IN ADDITION TO THE RECOMMENDED SEQUENCE. |
|---|---|---|
| 11 | Gray | Not stocked by CLS Community Collection Sites, but is stocked in Acute Care locations. Contains Sodium Fluoride and Potassium Oxalate anticoagulant |

Figure 27:
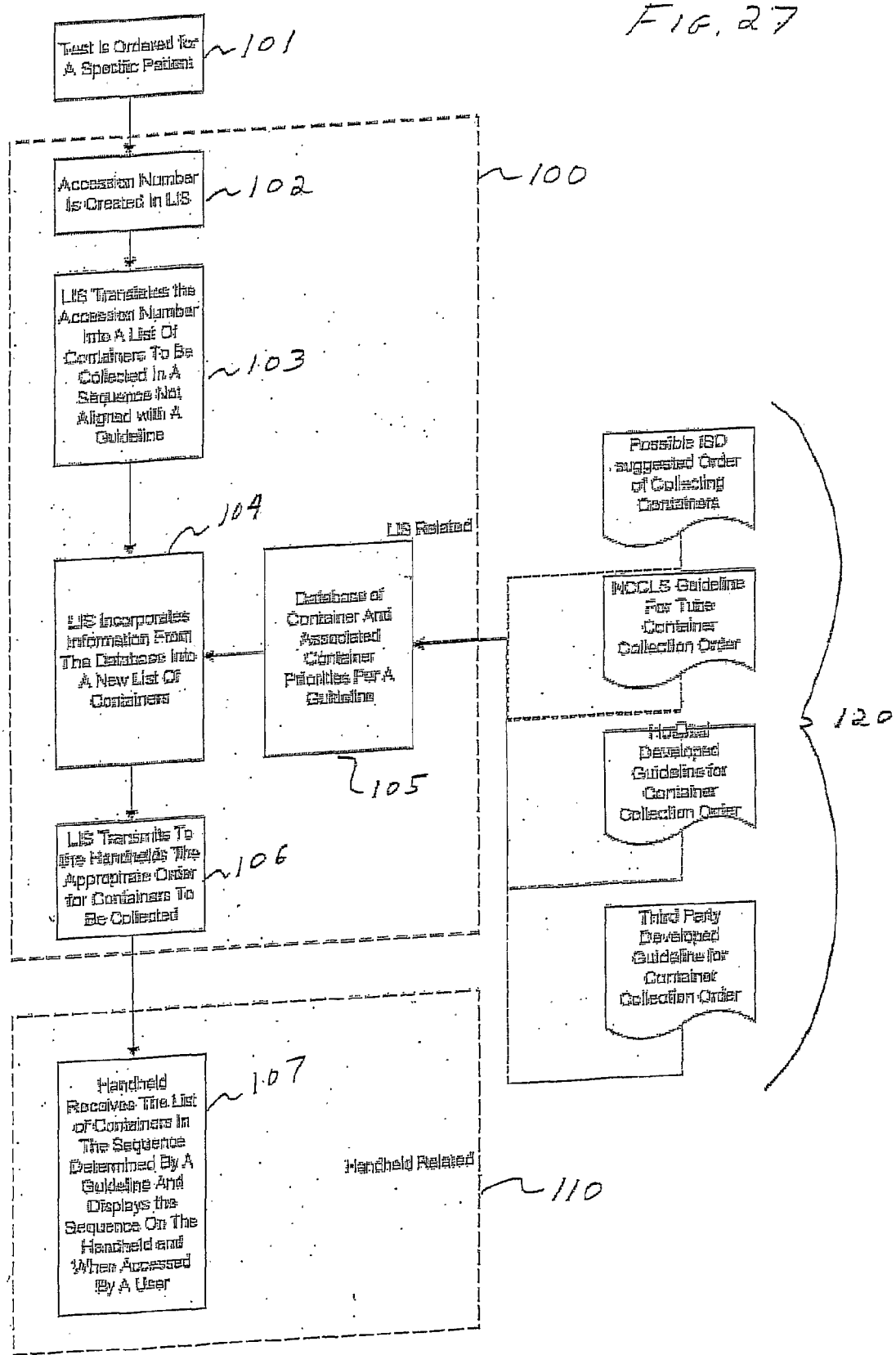
FIGS. 27 through 29 are flow charts depicting different system architectures for systems using the present invention.
Figure 28:
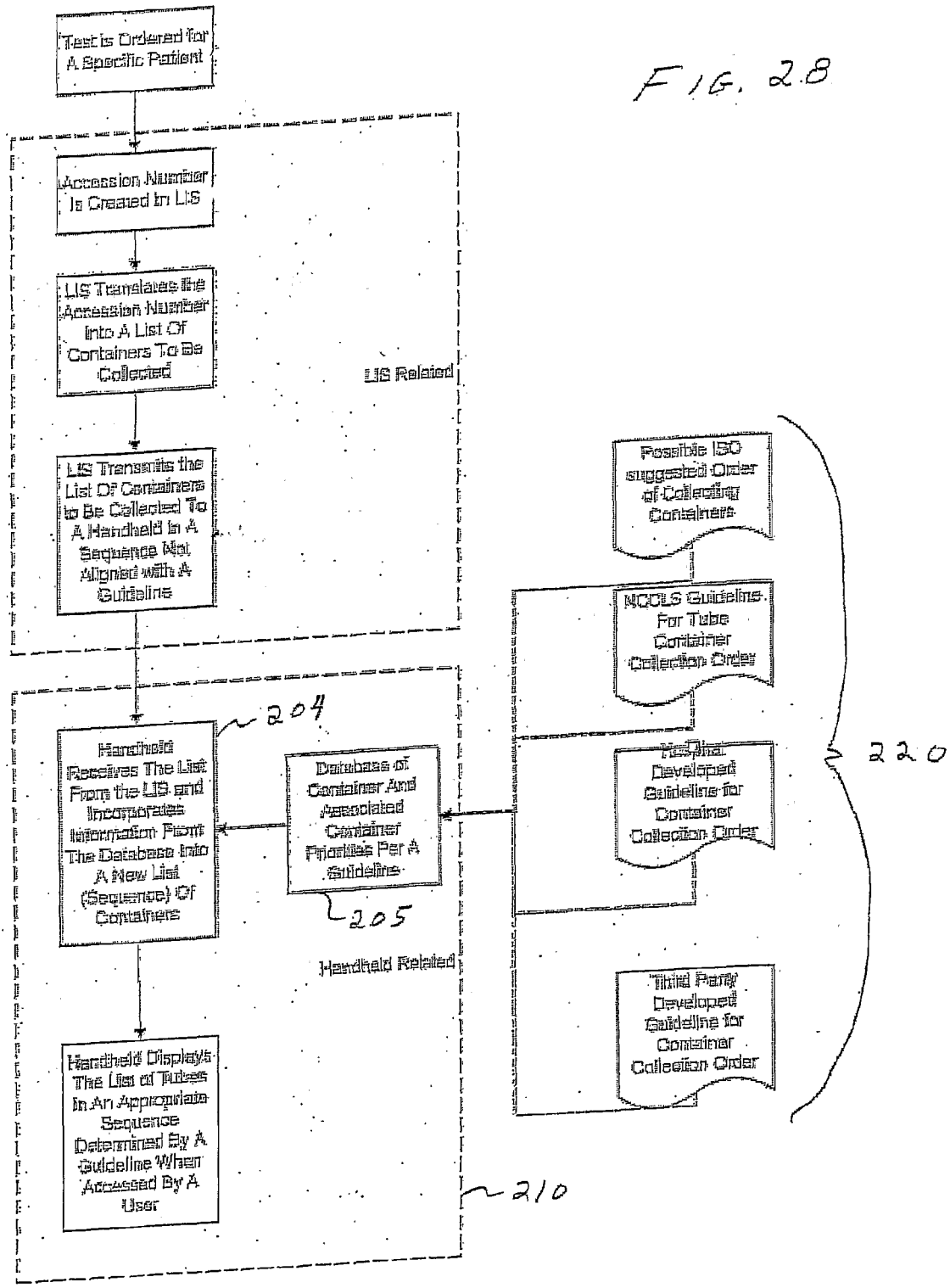
Figure 29:
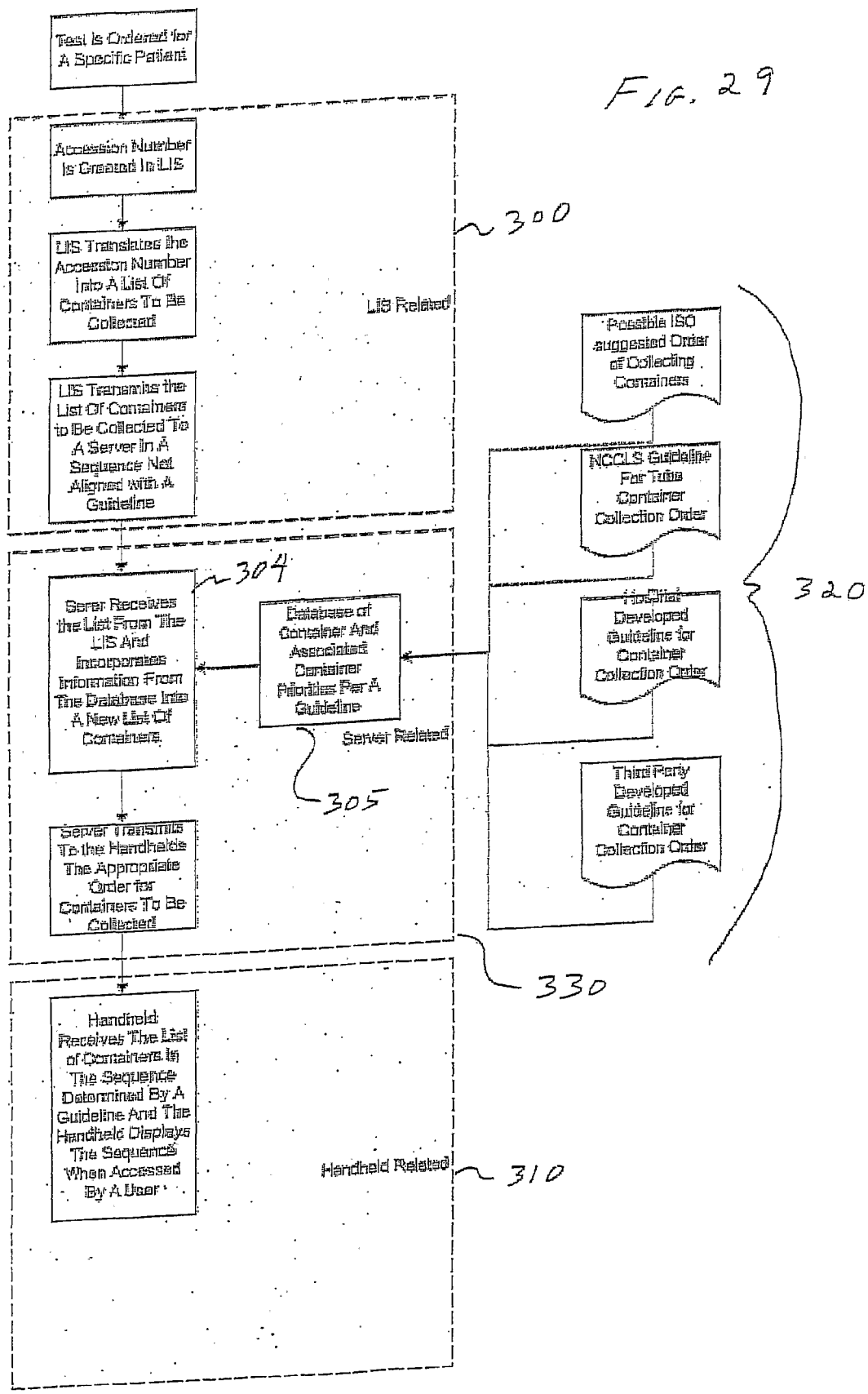

FIGS. 27, 28 and 29 more clearly show the systems described above based on the present invention. As shown, each system provides guidelines regarding the "order of draw" that are accessed and used to provide the handheld with a proper list of containers in a sequence that is required for collection. Each FIGS. 27, 28 and 29 shows a different architecture for the system. For example, FIG. 27 shows a system wherein LIS 100 receives guidelines for collection order 120 in a database 105 of container and associated container priorities and then uses that database 105 to create 104 a new list of containers from a list that was translated from an accession number into a list. As shown in FIG. 27, the system includes the following steps. First, a test is ordered for a specific patient 101, an accession number is created in the LIS 102, and then the LIS translates the accession number into a list of containers to be collected in a sequence not aligned with the guidelines 103. The LIS incorporates 104 that list into a new list using the database 105 of container and associated container priorities per a guideline to create a new list of containers in alignment with the guideline. The LIS then transmits 106 to the handheld the proper order for containers to be collected. In the last step 107, the handheld 110 receives the list of containers in the sequence determined by the guideline and displays the sequence on the handheld when accessed by a user. The system shown in FIG. 28 is very similar to the system shown in FIG. 27. However, the step of incorporating information from the database into a new list 204 is now performed by handheld 210 and the database 205 of container and associated container priorities per a guideline is stored in handheld 210, such that handheld 210 directly accesses guidelines 220 and displays 204 the list of tubes in the appropriate sequence. Finally, FIG. 29 shows a system in which a server 330 resides between LIS 300 and handheld 310 and the features of incorporating 304 and storing the database 305 are both provided by server 330.

In one embodiment applicable to blood collection tubes, a test might be sent from the LIS to the handheld, where the test does not call for a serum tube (red top), but does call for a coagulation tube (light blue top). Although this situation does not specifically call for a serum tube, a further embodiment of the present invention may indicate to the user to use a discard tube. Without using a discard tube, there is a possibility that tissue thromboplastin can contaminate the coagulation tube specimen during the venipuncture. To avoid this, the phlebotomist or nurse is usually told to use a serum tube (red top) and discard the tube in an appropriate disposal container commonly found in hospitals for medical waste prior to drawing the coagulation tube. To encourage the following of this procedure, the invention offers an embodiment wherein the server communicates to the handheld information for the user to use during collection. For example, if a test is ordered where the test does not call for a serum tube (red top), but does call for a coagulation tube this occurs, the server or the LIS might perform one of the following events:

1. Present indicia on the handheld that communicates to the user that a "discard tube" or plain serum tube should be drawn prior to the coagulation tube.

2. Add a discard tube to the list of tubes to be drawn. In one embodiment, this would be displayed as a red-top tube. In another embodiment, this would be displayed as a "discard tube" or equivalent thereof.

A further embodiment includes a provision for after collection and upon scanning the tubes, a tube with indicia such as a barcode that is read by the handheld scanner element should deliver a message to the user that the tube is to be discarded and not sent to the lab. This could be accomplished by the scanner producing an audible alert to the user, a message display on the handheld, or by not printing a new tube label upon scanning of the tube wherein scanning of tubes on the patient's list to be drawn would print from a printer in digital or analog communication with the handheld, directly or indirectly.

In another embodiment of the present invention, the LIS might send mnemonics that correlate to microcollection tubes used for capillary blood collection. Microcollection tubes do not have a vacuum to draw blood into the container, for they rely on capillary action and gravity to fill the specimen container. Also, capillary blood collection technique is traditionally performed by lancing through the capillary bed of a patient's finger or heel, rather than accessing the patient' veins. Lancing the patient's skin allows for blood to bead into drops on the patient's skin surface, and thus allows for the microcollection container to filled by a scooping method performed by the nurse or by the use of gravity wherein the tube catches drops of blood falling from the patient's skin. Should the LIS sent to the handheld (directly or indirectly through a server) mnemonics that correlate to microcollection containers, the order of draw that gets shown on the handheld screen for one patient might deviate from that used for evacuated blood collection systems. Therefore, a system would recognize that the mnemonics relate to capillary blood collection, and thus may use a different set of collection priority to establish the sequence presented to the user.

In one embodiment, the handheld displays capillary collection containers in the following order:

1. EDTA

2. Additive tubes for whole blood

3. Serum tubes

As stated above, the system may provide a default NCCLS sort order for each product. The NCCLS sort order requires a container to be mapped to products that have a NCCLS priority. If one container is mapped to at least two products and those products have different NCCLS priorities, then the container shall be listed using the lower NCCLS priority (the higher number).

Example

The container mappings look like:

| Product | NCCLS Priority | Container |
|---|---|---|
| Product 2 | 4 | LAV5 |
| Product 3 | 3 | BLUE |
| Product 4 | 4 | GREEN |
|  | 2 | RED |
| Product 5 | 2 | RED |

Patient 1 contains 5 orders with the same accession number:

| Priority | Time | Container | Tests |
|---|---|---|---|
| S | 06:00 | GREEN | LYTES |
| S | 06:00 | LAV5 | CBC |
| S | 06:00 | GREEN | REFX |
| S | 06:00 | RED | METB |
| S | 06:00 | BLUE | PT, PTT |

For Patient 1, the orders would be displayed on the Order List Screen as:

| Priority | Time | Container | Tests |
|---|---|---|---|
| S | 06:00 | RED | METB |
| S | 06:00 | BLUE | PT PTT |
| S | 06:00 | LAV5 | CBC |
| S | 06:00 | GREEN | REFX |
| S | 06:00 | GREEN | LYTES |

In all embodiments of the invention, the order of tubes drawn must be executed by accessing a database. In all embodiments of the invention, the types of tubes must be determinate. Therefore, either the system can receive a test and then construct which tubes are connected to that test and finally sequence the tubes displayed on the handheld. Otherwise, the system can receive a list of tubes that an LIS system already identified as being required, wherein the system merely corrects or ensures that the sequence of tubes to be drawn are accurate to a standard.

Embodiments of the present invention have been described, and it should be understood that the invention is not limited to the details thereof. Various modifications and substitutions have been suggested in the foregoing description, and others will occur to those of ordinary skill in the art. All such substitutions are intended to be embraced within the scope of the invention as defined in the appended claims.

What is claimed is:

1. A handheld point of care specimen collection support system comprising:
a handheld device, comprising at least one processing device, configured to receive an order initiated by a user, for specimen collection to be performed for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed;
a processor configured to receive information relating to collection of at least one patient derived specimen;
an interface configured to display at least a portion of the received information and data indicating a received order; and
an output device configured to output a message, based at least in part on the at least a portion of the information, indicating that at least a portion of said collection has not been completed.

2. A handheld point of care specimen collection support system comprising:
a handheld device, comprising at least one processing device, configured to receive an order initiated by a user, for specimen collection to be performed for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed;
a processor configured to receive information relating to collection of at least one patient derived specimen;
an interface configured to display at least a portion of the received information and data indicating a received order; and
an output device configured to output special instructions associated with the collection based on at least in part a portion of the information.

3. The system of claim 2, wherein the special instructions relate to at least one test to be performed on the at least one specimen and said button comprises a displayed image element and
said handheld device enables said user to associate a selected variance identifier with a particular specimen collection.

4. The system of claim 2, wherein the special instructions relate to at least one container used for the collection.

5. A handheld system comprising:
a handheld device, comprising at least one processing device, configured to receive an order initiated by a user, for specimen collection to be performed for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed and to associate a selected variance identifier with a particular specimen collection;
a processor configured to receive information relating to collection of at least one patient derived specimen associated with a received order;
an interface configured to display at least a portion of the information; and
an input device for entering workload information regarding at least a portion of the collection that has been filled or attempted to be filled based on at least in part a portion of the information.

6. A handheld point of care specimen collection support system comprising:
a handheld device, comprising at least one processing device, configured to receive an order initiated by a user, for specimen collection to be performed for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed;
a processor configured to receive information relating to collection of at least one patient derived specimen associated with a received order;
an interface configured to display at least a portion of the information; and
an input device configured to input data regarding cancellation of at least a portion of the collection that is attempted based on at least in part a portion of the information.

7. A handheld device and user interface for use in collecting specimen samples and including at least one processing device, comprising:
a handheld device, comprising at least one processing device, configured to receive an order initiated by a user, for specimen collection to be performed for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed;
an interface configured to receive at least one guideline relating to received sequence in which specimen samples should be collected; and
an output screen for displaying a sequential list showing the sequence in which the specimen samples should be collected based on the at least one guideline.

8. A system for collecting specimen samples, comprising:
a handheld device, comprising at least one processing device, configured to receive an order initiated by a user, for specimen collection to be performed for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed;
an interface configured to receive information regarding priority associated with specimen sample containers to be filled for a received order; and
a handheld device output screen segregated into a number of screen areas, at least one of the screen areas relating to showing specimen sample containers to be filled,
wherein said at least one screen area relating to showing specimen sample containers to be filled includes information regarding priority associated with the specimen sample containers to be filled.

9. A method for specimen collection, comprising:
employing at least one processing device configured for,
receiving an order initiated by a user, for specimen collection to be performed for a patient and indicating a selection of specimen collection containers to be collected;
enabling in response to user selection of a button, a user to enter data identifying a deviation event occurred as a result of failure to complete specimen collection for the patient;
enabling said user to select a variance identifier identifying said deviation event and identifying specimen collection was unable to be completed;
accessing a database that associates priority of collection to each of said specimen collection containers;
sorting the specimen collection containers based on said priority; and
displaying said priority on a screen of a handheld device.

10. The method of claim 9, wherein said sorting of said specimen collection containers is performed by an algorithm resident in a laboratory information system.

11. The method of claim 9, wherein said sorting of said specimen collection containers is performed by an algorithm resident in the handheld device.

12. The method of claim 9, wherein said sorting of said specimen collection containers is performed by an algorithm resident in a server capable of electronic communication with said handheld device.

13. A handheld device and user interface for use in collecting specimen samples and comprising at least one processing device, comprising:
a handheld device, comprising at least one processing device, configured to receive an order initiated by a user, for specimen collection to be performed for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed and to associate a selected variance identifier with a particular specimen collection;
an interface configured to receive information regarding a variance to instructions associated with a filled specimen sample container and received order; and
an output screen segregated into a number of screen areas, at least one of the screen areas related to a window showing specimen sample containers that have been filled,
wherein said at least one screen areas showing specimen sample containers that have been filled includes the information regarding the variance.

14. A system for collecting specimen samples comprising at least one processing device, comprising:
a handheld device, comprising at least one processing device, configured to receive an order initiated by a user, for specimen collection to be performed for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed and to associate a selected variance identifier with a particular specimen collection;
an output configured to display sample collection and management information and data indicating a received order to the user; and
a processor configured to indicate that a portion of specimen samples have been collected.

15. A handheld communication and point of care specimen collection support device comprising at least one processing device, comprising:
at least one processor configured to receive an order for specimen collection for a patient and enabling in response to user selection of a button, a user to enter data identifying a deviation event occurred as a result of failure to complete specimen collection for the patient and enabling said user to select a variance identifier identifying said deviation event and identifying specimen collection was unable to be completed;
a display unit coupled to a processor having access to a computer-readable storage medium having stored therein computer-readable instructions, which, when executed by the processor, cause the processor to display a user interface on the display of the handheld communication device, said user interface comprising:
a main screen communicating data indicating at least one test collection specimen container to be collected from a patient associated with a received order; and
an icon displayed at least temporarily on said screen, whereby activating the icon informs the handheld communication device to print a label indicating that said test collection specimen container was not collected.

16. A method for collection of sample specimens, comprising:
employing at least one processing device configured for,
receiving an order for specimen collection for a patient;
enabling in response to user selection of a button, a user to enter data identifying a deviation event occurred as a result of failure to complete specimen collection for the patient;
enabling said user to select a variance identifier identifying said deviation event and identifying specimen collection was unable to be completed and to associate a selected variance identifier with a particular specimen collection;
reading at least one identification code associated with a received order and at least one of the following: at least one container and at least one patient identification tag;
receiving a set of rules for specimen collection associated with the at least one identification code;
determining whether the set of rules associated with the at least one identification code is followed; and
outputting a message that indicates when the set of rules has not been followed.

17. The method of claim 16, wherein said identification code is a barcode.

18. The method of claim 16, further comprising:
displaying instructions on said portable handheld device if said set of rules has not been followed.

19. The method of claim 16, further comprising communicating a notification to a remote location if said set of rules has not been followed.

20. A method of generating an incomplete specimen collection order, comprising:
employing at least one processing device configured for,
sending to a handheld device an order including a specimen collection protocol;
receiving an order for specimen collection for a patient;
enabling in response to user selection of a button, a user to enter data identifying a deviation event occurred as a result of failure to complete specimen collection for the patient;
enabling said user to select a variance identifier identifying said deviation event and identifying specimen collection was unable to be completed;
displaying the received order;
determining whether the specimen collection protocol was performed in accordance with said order; and
communicating an incomplete collection message when the specimen collection protocol was not performed in accordance with said order.

21. A system for point of care specimen collection support and for printing identity labels in a healthcare setting, comprising:
a scanner for scanning a patient label;
a processor enabling in response to user selection of a button, a user to enter data identifying a deviation event occurred as a result of failure to complete specimen collection for the patient and enabling said user to select a variance identifier identifying said deviation event and identifying specimen collection was unable to be completed and to associate a selected variance identifier with a particular specimen collection;
a processor communicating patient data stored in a handheld device with a database, the database including patient demographic information related to said patient; and
a printer in communication with said handheld device,
wherein said handheld device instructs said printer to generate an identity label including patient demographic information if the patient data in the handheld device has patient demographic information corresponding to a patient label scanned by said scanner.

* * * * *